(12) United States Patent
Zheng

(10) Patent No.: US 9,343,684 B2
(45) Date of Patent: May 17, 2016

(54) SUBSTITUTED BISARYLOXYBIPHENYL COMPOUNDS FOR USE IN LIGHT-EMITTING DEVICES

(71) Applicant: NITTO DENKO CORPORATION, Osaka (JP)

(72) Inventor: Shijun Zheng, San Diego, CA (US)

(73) Assignee: NITTO DENKO CORPORATION, Osaka (JP)

( * ) Notice: Subject to any disclaimer, the term of this patent is extended or adjusted under 35 U.S.C. 154(b) by 389 days.

(21) Appl. No.: 13/848,675

(22) Filed: Mar. 21, 2013

(65) Prior Publication Data

US 2014/0284554 A1  Sep. 25, 2014

(51) Int. Cl.
| | |
|---|---|
| *H01L 51/50* | (2006.01) |
| *H01L 51/00* | (2006.01) |
| *C07F 15/00* | (2006.01) |
| *C07C 217/92* | (2006.01) |
| *C07F 7/08* | (2006.01) |
| *C07D 209/86* | (2006.01) |
| *C09K 11/06* | (2006.01) |

(52) U.S. Cl.
CPC ............ *H01L 51/006* (2013.01); *C07C 217/92* (2013.01); *C07D 209/86* (2013.01); *C07F 7/0818* (2013.01); *C07F 15/0033* (2013.01); *C09K 11/06* (2013.01); *H01L 51/0059* (2013.01); *H01L 51/0072* (2013.01); *C09K 2211/1014* (2013.01); *H01L 51/0085* (2013.01); *H01L 51/5012* (2013.01); *H01L 51/5056* (2013.01); *H01L 2251/308* (2013.01)

(58) Field of Classification Search
None
See application file for complete search history.

(56) References Cited

U.S. PATENT DOCUMENTS

| | | | |
|---|---|---|---|
| 5,480,765 A * | 1/1996 | Yanagihara | B41M 5/3375 430/332 |
| 6,280,859 B1 * | 8/2001 | Onikubo et al. | 428/690 |
| 2012/0214269 A1 | 8/2012 | Harding | |

FOREIGN PATENT DOCUMENTS

| | | |
|---|---|---|
| DE | 102006010915 | 9/2007 |
| JP | 2010-251633 A | 11/2010 |
| WO | 2008131750 | 11/2008 |

OTHER PUBLICATIONS

Schwartz, G. et al., "Triplet Harvesting in Hybrid White Organic Light-Emitting Diodes", Adv. Funct. Matter, vol. 19, pp. 1319-1333, 2009.

\* cited by examiner

*Primary Examiner* — Gregory Clark
(74) *Attorney, Agent, or Firm* — K&L Gates LLP; Brent A. Johnson; Louis C. Cullman

(57) ABSTRACT

Compounds according to Formula 1 may be used as host materials, hole-transfer materials, hole-injecting materials, or for other purposes in electronic devices such as in organic light-emitting devices.

19 Claims, 4 Drawing Sheets

SUBSTITUTED BISARYLOXYBIPHENYL COMPOUNDS FOR USE IN LIGHT-EMITTING DEVICES

BACKGROUND

1. Field of the Invention

The embodiments relate to compounds such as substituted biaryl ring systems for use in light-emitting devices.

2. Description of the Related Art

Organic light-emitting devices (OLEDs) have been widely developed for flat panel displays, and are rapidly moving toward solid state lighting (SSL) applications. Some believe that a white OLED device with greater than 1,500 lm, a color rendering index (CRI) greater than 70, and an operating time greater than 10,000 hours at 1,000 lm/w may be useful in SSL applications. In order to reduce the driving voltage of an OLED device and extend the operational lifetime, it may be helpful to develop new high performance electron transport materials.

SUMMARY

Some embodiments include a compound represented by Formula 1:

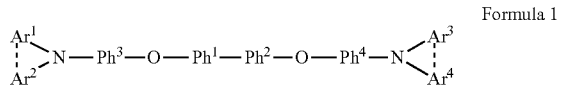

Formula 1 wherein each dashed line is independently an optional bond; $Ph^1$, $Ph^2$, $Ph^3$, and $Ph^4$, are independently optionally substituted p-phenylene; and $Ar^1$, $Ar^2$, $Ar^3$, and $Ar^4$, are independently optionally substituted phenyl or optionally substituted naphthyl. In some embodiments, each substituent of $Ar^1$, $Ar^2$, $Ar^3$, and $Ar^4$ is independently $C_{1-6}$ alkyl.

Some embodiments include an organic light-emitting device comprising a compound described herein.

Some embodiments include a composition comprising a compound described herein. Such a composition may be useful for transporting holes or injecting holes.

Some embodiments include a method of transporting holes between layers comprising: disposing a composition comprising a compound described herein between a first layer and a second layer so that the composition is capable of transporting holes from the first layer to the second layer; and providing an electrical potential difference between the first layer and the second layer.

Some embodiments include a method of transporting holes between layers comprising: providing an electrical potential difference between a first layer and a second layer through a composition comprising a compound described herein.

DETAILED DESCRIPTION

Figure 1:
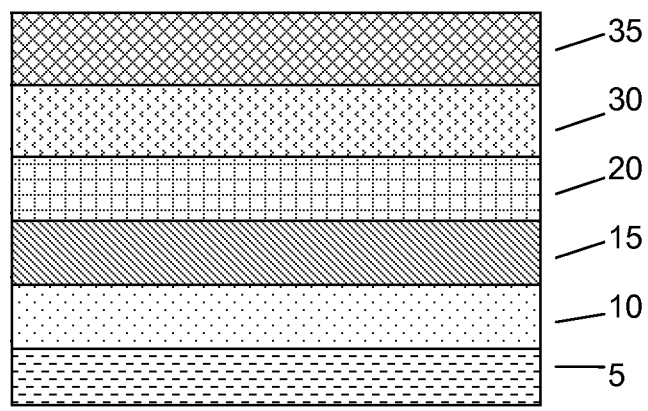
FIG. 1 is schematic diagram of an embodiment of an organic light-emitting diode (OLED).

Unless otherwise indicated, when a chemical structural feature such as alkyl or aryl is referred to as being "optionally substituted," it is meant that the feature may have no substituents (i.e. be unsubstituted) or may have one or more substituents. A feature that is "substituted" has one or more substituents. The term "substituent" has the ordinary meaning known to one of ordinary skill in the art. In some embodiments, the substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 200 g/mol, 15 g/mol to 300 g/mol, or 15 g/mol to 500 g/mol. In some embodiments, the substituent comprises: 0-30, 0-20, 0-10, or 0-5 carbon atoms; and 0-30, 0-20, 0-10, or 0-5 heteroatoms independently selected from: N, O, S, Si, F, Cl, Br, or I; provided that the substituent comprises at least one atom selected from: C, N, O, S, Si, F, Cl, Br, or I. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

The structures of some of the moieties referred to herein are depicted below. These moieties may be unsubstituted, as shown below, or a substituent may independently be in any position normally occupied by a hydrogen atom when the moiety is unsubstituted.

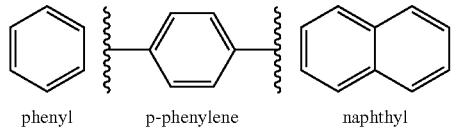

phenyl    p-phenylene    naphthyl

As used herein the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

As used herein, the term "alkoxy" includes —O-alkyl, such as —$OCH_3$, —$OC_2H_5$, —$OC_3H_7$ (e.g. propoxy isomers such as isopropoxy, n-propoxy, etc.), —OC$_4$H$_9$ (e.g. butyoxy isomers), —OC$_5$H$_{11}$ (e.g. pentoxy isomers), —OC$_6$H$_{13}$ (e.g. hexoxy isomers), —OC$_7$H$_{15}$ (e.g. heptoxy isomers), etc.

As used herein, a dashed line represents an optional bond. For example, with respect to the dashed lines depicted in Formula 1, compounds according to Formula 2, Formula 3, and Formula 4, are included.

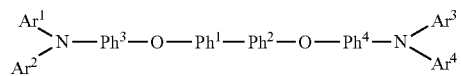

Formula 2

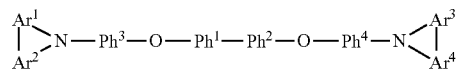

Formula 3

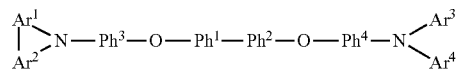

Formula 4

The term "low work function" has the ordinary meaning known to one of ordinary skill in the art, and may include a measure of the minimum energy required to extract an electron from the surface of the metal.

The term "high work function" has the ordinary meaning known to one of ordinary skill in the art, and may include a metal or alloy that easily injects holes and typically has a work function greater than or equal to about 4.5.

The term "low work function metal" has the ordinary meaning known to one of ordinary skill in the art, and may include a metal or alloy that easily loses electrons and typically has a work function less than about 4.3.

The expression "white light-emitting" has the ordinary meaning known to one of ordinary skill in the art, and may include a material is that emits white light. In some embodiments, white light may have the approximate CIE color coordinates (X=1/3, Y=1/3/ ). The CIE color coordinates (X=1/3, Y=1/3) may be referred to as the achromatic point. The X and Y color coordinates may be weights applied to the CIE primaries to match a color. A more detailed description of these terms may be found in CIE 1971, International Commission on Illumination, Colorimetry: Official Recommendations of the International Commission on Illumination, Publication CIE No. 15 (E-1.3.1) 1971, Bureau Central de la CIE, Paris, 1971 and in F. W. Billmeyer, Jr., M. Saltzman, Principles of Color Technology, 2nd edition, John Wiley & Sons, Inc., New York, 1981, both of which are hereby incorporated by reference in their entireties. The color rendering index (CRI) refers to the ability to render various colors and has values ranging from 0 to 100, with 100 being the best.

Formula 5

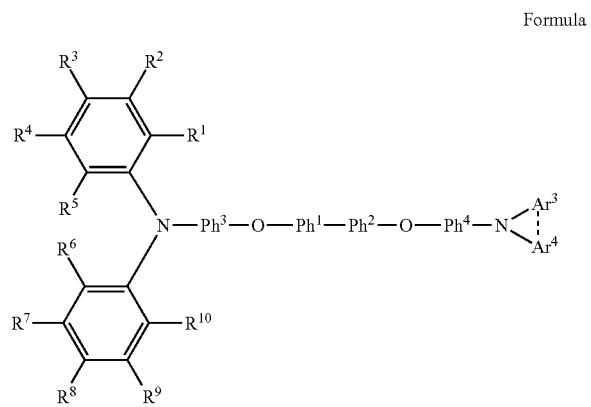

Formula 6

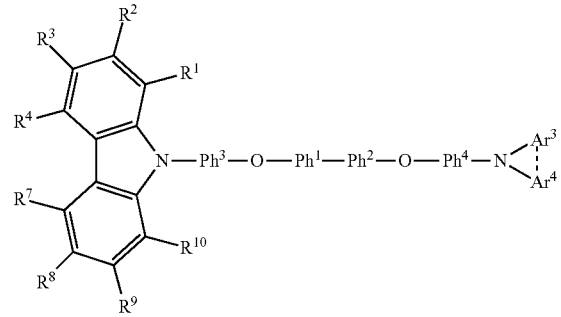

Formula 7

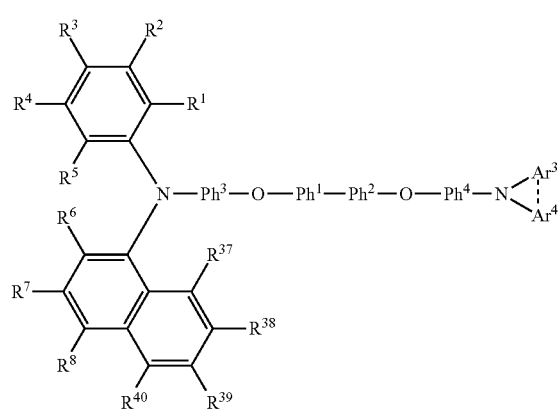

Formula 8

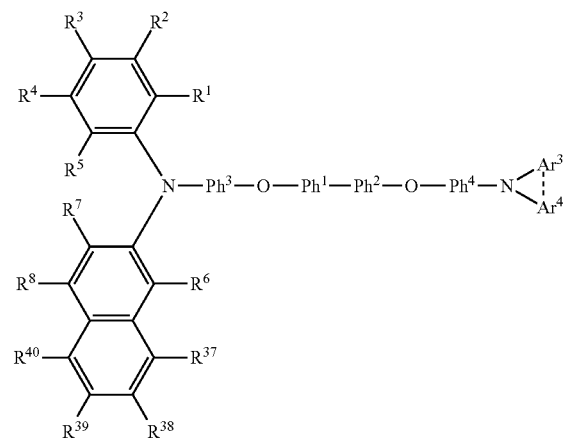

-continued
Formula 9
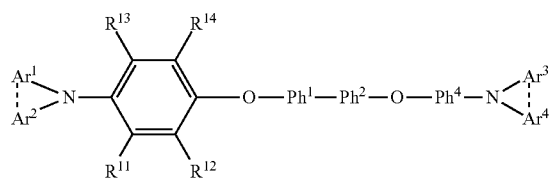
Formula 10
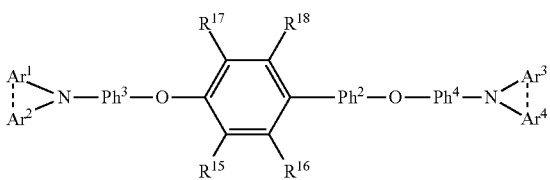
Formula 11
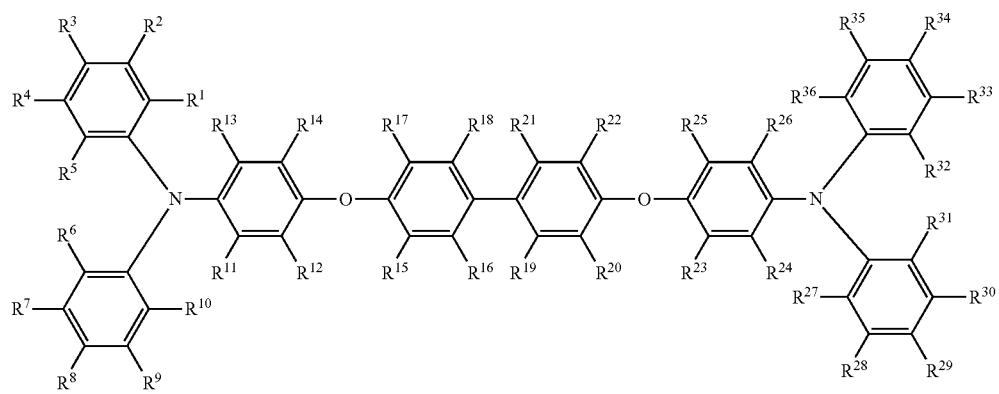
Formula 12
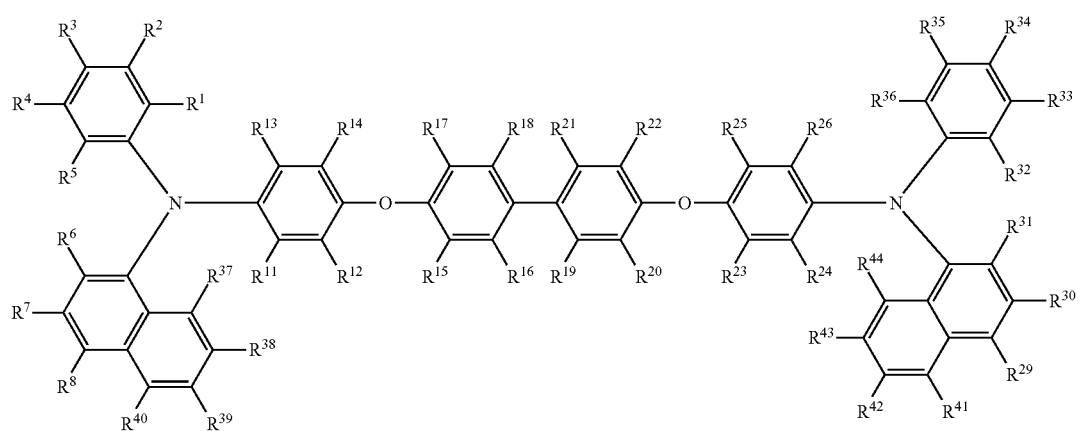
Formula 13
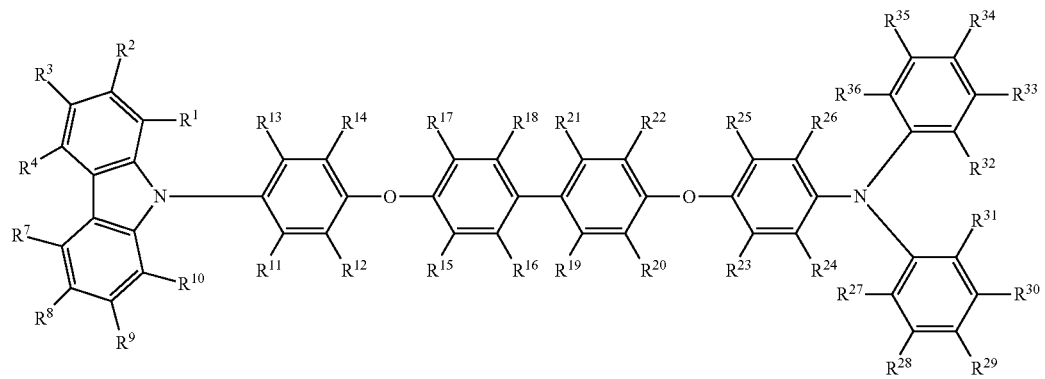

-continued

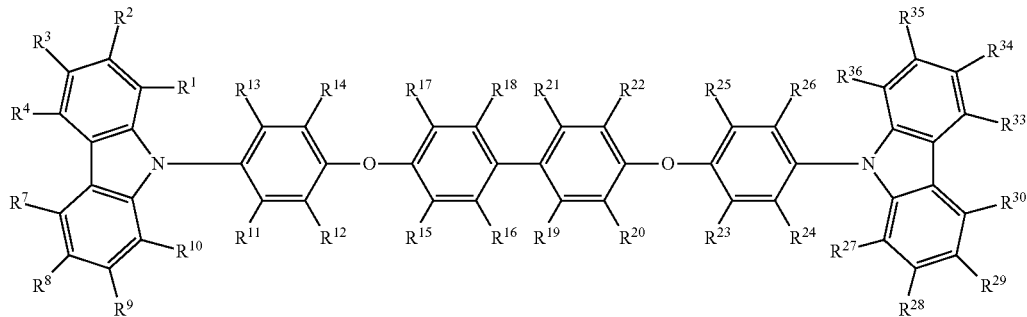

Formula 14

With respect to any relevant formula above, Ph$^1$ may be optionally substituted p-phenylene. If Ph$^1$ is substituted, it may have 1, 2, 3, or 4 substituents, wherein each substituent may have a molecular weight of about 15 g/mol to 50 g/mol, 15 g/mol to 100 g/mol, 15 g/mol to about 200 g/mol, or about 15 g/mol to 500 g/mol. In some embodiments, any or all substituents may be independently selected from: $C_{1-12}$ alkyl, including methyl, ethyl, propyl isomers, cyclopropyl, butyl isomers, cyclobutyl isomers, pentyl isomers, cyclopentyl isomers, hexyl isomers, cyclohexyl isomers, heptyl isomers, cycloheptyl isomers, octyl isomers, cyclooctyl isomer, etc.; $C_{1-12}$ alkoxy such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; F; Cl; Br; I; $C_{1-3}$ fluoroalkyl such as $CH_2F$, $CHF_2$, $CF_3$, $C_2F_5$, $C_3F_7$, etc.; OH; CN; $NO_2$, $NR^AR^B$; $COR^A$; $CO_2R^A$; $OCOR^A$; $NR^ACOR^B$; $CONR^AR^B$; etc.

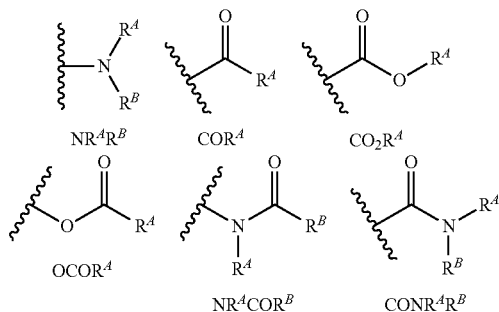

In some embodiments, Ph$^1$ may be:

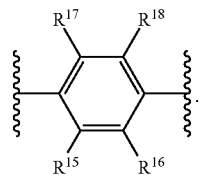

Each $R^A$ may independently be H, or $C_{1-12}$ alkyl, including: linear or branched alkyl having a formula $C_aH_{a+1}$, or cycloalkyl having a formula $C_aH_a$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{17}$, $C_8H_{15}$, $C_9H_{17}$, $C_{10}H_{19}$, etc. In some embodiments, each $R^A$ may independently be H, $C_{1-3}$ alkyl, or $C_{1-6}$ alkyl.

Each $R^B$ may independently be H, or $O_{1-12}$ alkyl, including: linear or branched alkyl having a formula $C_aH_{a+1}$, or cycloalkyl having a formula $C_aH_a$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{17}$, $C_8H_{15}$, $C_9H_{17}$, $C_{10}H_{19}$, etc. In some embodiments, each $R^B$ may independently be H, $C_{1-3}$ alkyl, or $C_{1-6}$ alkyl.

With respect to any relevant formula above, Ph$^2$ may be optionally substituted p-phenylene. If Ph$^2$ is substituted, it may have 1, 2, 3, or 4 substituents, wherein each substituent may have a molecular weight of 15 g/mol to 50 g/mol, 15 g/mol to 100 g/mol, 15 g/mol to about 200 g/mol, or 15 g/mol to 500 g/mol. In some embodiments, any or all substituents may be independently selected from: $C_{1-12}$ alkyl, including methyl, ethyl, propyl isomers, cyclopropyl, butyl isomers, cyclobutyl isomers, pentyl isomers, cyclopentyl isomers, hexyl isomers, cyclohexyl isomers, heptyl isomers, cycloheptyl isomers, octyl isomers, cyclooctyl isomer, etc.; $C_{1-12}$ alkoxy such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; F; Cl; Br; I; $C_{1-3}$ fluoroalkyl such as $CH_2F$, $CHF_2$, $CF_3$, $C_2F_5$, $C_3F_7$, etc.; OH; CN; $NO_2$, $NR^AR^B$; $COR^A$; $CO_2R^A$; $OCOR^A$; $NR^ACOR^B$; $CONR^AR^B$; etc.

In some embodiments, Ph$^2$ may be:

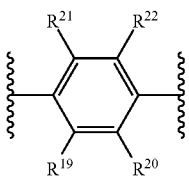

With respect to any relevant formula above, Ph$^3$ may be optionally substituted p-phenylene. If Ph$^3$ is substituted, it may have 1, 2, 3, or 4 substituents, wherein each substituent may have a molecular weight of 15 g/mol to 50 g/mol, 15 g/mol to 100 g/mol, 15 g/mol to about 200 g/mol, or 15 g/mol to 500 g/mol. In some embodiments, any or all substituents may be independently selected from: $C_{1-12}$ alkyl, including methyl, ethyl, propyl isomers, cyclopropyl, butyl isomers, cyclobutyl isomers, pentyl isomers, cyclopentyl isomers, hexyl isomers, cyclohexyl isomers, heptyl isomers, cycloheptyl isomers, octyl isomers, cyclooctyl isomer, etc.; $C_{1-12}$ alkoxy such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; F; Cl; Br; I; $C_{1-3}$ fluoroalkyl such as $CH_2F$, $CHF_2$, $CF_3$, $C_2F_5$, $C_3F_7$, etc.; OH; CN; $NO_2$, $NR^A R^B$; $COR^A$; $CO_2R^A$; $OCOR^A$; $NR^A COR^B$; $CONR^A R^B$; etc.

In some embodiments, $Ph^3$ may be:

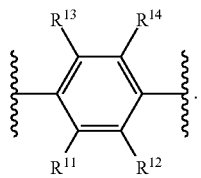

With respect to any relevant formula above, $Ph^4$ may be optionally substituted p-phenylene. If $Ph^4$ is substituted, it may have 1, 2, 3, or 4 substituents, wherein each substituent may have a molecular weight of 15 g/mol to 50 g/mol, 15 g/mol to 100 g/mol, 15 g/mol to about 200 g/mol, or 15 g/mol to 500 g/mol. In some embodiments, any or all substituents may be independently selected from: $C_{1-12}$ alkyl, including methyl, ethyl, propyl isomers, cyclopropyl, butyl isomers, cyclobutyl isomers, pentyl isomers, cyclopentyl isomers, hexyl isomers, cyclohexyl isomers, heptyl isomers, cycloheptyl isomers, octyl isomers, cyclooctyl isomer, etc.; $C_{1-12}$ alkoxy such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; F; Cl; Br; I; $C_{1-3}$ fluoroalkyl such as $CH_2F$, $CHF_2$, $CF_3$, $C_2F_5$, $C_3F_7$, etc.; OH; CN; $NO_2$, $NR^A R^B$; $COR^A$; $CO_2R^A$; $OCOR^A$; $NR^A COR^B$; $CONR^A R^B$; etc.

In some embodiments, $Ph^4$ may be:

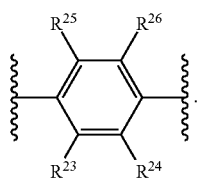

In some embodiments, $Ph^1$, $Ph^2$, $Ph^3$, and $Ph^4$ are unsubstituted. In other embodiments, all substituents of $Ph^1$, $Ph^2$, $Ph^3$, and $Ph^4$ may have a molecular weight of 15 g/mol to 50 g/mol, 15 g/mol to 150 g/mol, or 15 g/mol to 500 g/mol; and/or all substuents of $Ph^1$, $Ph^2$, $Ph^3$, and $Ph^4$ may be independently selected from: $C_{1-12}$ alkyl, including methyl, ethyl, propyl isomers, cyclopropyl, butyl isomers, cyclobutyl isomers, pentyl isomers, cyclopentyl isomers, hexyl isomers, cyclohexyl isomers, heptyl isomers, cycloheptyl isomers, octyl isomers, cyclooctyl isomer, etc.; $C_{1-12}$ alkoxy such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, etc.; F; Cl; Br; I; $C_{1-3}$ fluoroalkyl such as $CH_2F$, $CHF_2$, $CF_3$, $C_2F_5$, $C_3F_7$, etc.; OH; CN; $NO_2$, $NR^A R^B$; $COR^A$; $CO_2R^A$; $OCOR^A$; $NR^A COR^B$; $CONR^A R^B$; etc.

With respect to any formula above, $Ar^1$ may be optionally substituted phenyl or optionally substituted naphthyl. In some embodiments, each substituent of a phenyl or naphthyl may have a molecular weight of 15 g/mol to 50 g/mol, 15 g/mol to 150 g/mol, or 15 g/mol to 500 g/mol. In some embodiments, each substituent may independently be $C_{1-6}$ alkyl, including methyl, ethyl, propyl isomers, cyclopropyl, butyl isomers, cyclobutyl isomers, pentyl isomers, cyclopentyl isomers, hexyl isomers, cyclohexyl isomers, etc.

In some embodiments, $Ar^1$ may be:

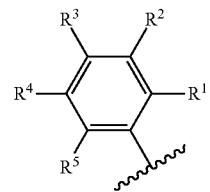

With respect to any formula above, $Ar^2$ may be optionally substituted phenyl or optionally substituted naphthyl. In some embodiments, each substituent of a phenyl or naphthyl may have a molecular weight of 15 g/mol to 50 g/mol, 15 g/mol to 150 g/mol, or 15 g/mol to 500 g/mol. In some embodiments, each substituent may independently be $C_{1-6}$ alkyl, including methyl, ethyl, propyl isomers, cyclopropyl, butyl isomers, cyclobutyl isomers, pentyl isomers, cyclopentyl isomers, hexyl isomers, cyclohexyl isomers, etc.

In some embodiments, $Ar^2$ may be:

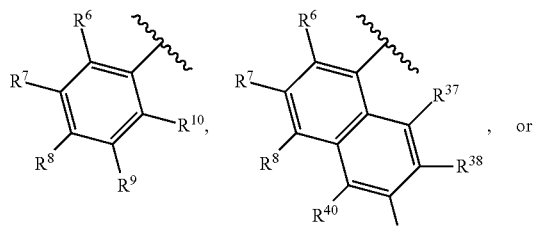

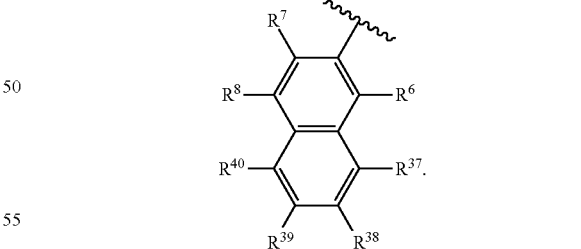

With respect to any formula above, $Ar^3$ may be optionally substituted phenyl or optionally substituted naphthyl. In some embodiments, each substituent of a phenyl or naphthyl may have a molecular weight of 15 g/mol to 50 g/mol, 15 g/mol to 150 g/mol, or 15 g/mol to 500 g/mol. In some embodiments, each substituent may independently be $C_{1-6}$ alkyl, including methyl, ethyl, propyl isomers, cyclopropyl, butyl isomers, cyclobutyl isomers, pentyl isomers, cyclopentyl isomers, hexyl isomers, cyclohexyl isomers, etc.

In some embodiments,

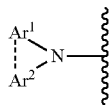

may be:

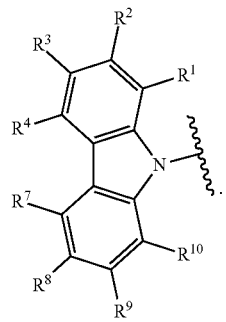

In some embodiments, Ar³ may be:

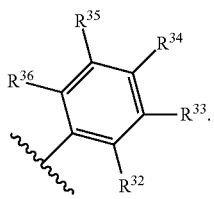

With respect to any formula above, Ar⁴ may be optionally substituted phenyl or optionally substituted naphthyl. In some embodiments, each substituent of a phenyl or naphthyl may have a molecular weight of 15 g/mol to 50 g/mol, 15 g/mol to 150 g/mol, or 15 g/mol to 500 g/mol. In some embodiments, each substituent may independently be $C_{1-6}$ alkyl, including methyl, ethyl, propyl isomers, cyclopropyl, butyl isomers, cyclobutyl isomers, pentyl isomers, cyclopentyl isomers, hexyl isomers, cyclohexyl isomers, etc.

In some embodiments, Ar⁴ may be:

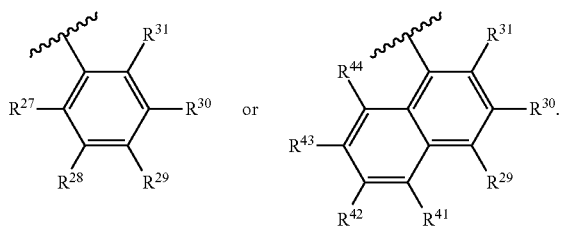

In some embodiments,

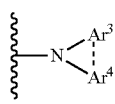

may be

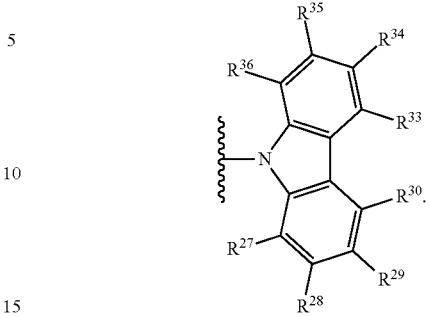

With respect to any relevant formula or structural depiction above, $R^1$ may be H or any substituent. Some non-limiting examples of $R^1$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^1$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^1$ may be H.

With respect to any relevant formula or structural depiction above, $R^2$ may be H or any substituent. Some non-limiting examples of $R^2$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^2$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^2$ may be H.

With respect to any relevant formula or structural depiction above, $R^3$ may be H or any substituent. Some non-limiting examples of $R^3$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^3$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^3$ may be H.

With respect to any relevant formula or structural depiction above, $R^4$ may be H or any substituent. Some non-limiting examples of $R^4$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^4$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^4$ may be H.

With respect to any relevant formula or structural depiction above, $R^5$ may be H or any substituent. Some non-limiting examples of $R^5$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^5$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^5$ may be H.

With respect to any relevant formula or structural depiction above, $R^6$ may be H or any substituent. Some non-limiting examples of $R^6$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^6$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^6$ may be H.

With respect to any relevant formula or structural depiction above, $R^7$ may be H or any substituent. Some non-limiting examples of $R^7$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^7$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^7$ may be H.

With respect to any relevant formula or structural depiction above, $R^8$ may be H or any substituent. Some non-limiting examples of $R^8$ may include $R^A$, F, Cl, CN, $OR^A$, $CF_3$, $NO_2$, $NR^A R^B$, $COR^A$, $CO_2R^A$, $OCOR^A$, etc. In some embodiments, $R^8$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^8$ may be H.

With respect to any relevant formula or structural depiction above, $R^9$ may be H or any substituent. Some non-limiting examples of $R^9$ may include $R^A$, F, Cl, CN, $OR^A$, $CF_3$, $NO_2$, $NR^A R^B$, $COR^A$, $CO_2R^A$, $OCOR^A$, etc. In some embodiments, $R^9$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^9$ may be H.

With respect to any relevant formula or structural depiction above, $R^{10}$ may be H or any substituent. Some non-limiting examples of $R^{10}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{10}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{19}$ may be H.

With respect to any relevant formula or structural depiction above, $R^{11}$ may be H or any substituent. Some non-limiting examples of $R^{11}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{11}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{11}$ may be H.

With respect to any relevant formula or structural depiction above, $R^{12}$ may be H or any substituent. Some non-limiting examples of $R^{12}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{12}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{12}$ may be H.

With respect to any relevant formula or structural depiction above, $R^{13}$ may be H or any substituent. Some non-limiting examples of $R^{13}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{13}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{13}$ may be H.

With respect to any relevant formula or structural depiction above, $R^{14}$ may be H or any substituent. Some non-limiting examples of $R^{14}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{14}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{14}$ may be H.

With respect to any relevant formula or structural depiction above, $R^{15}$ may be H or any substituent. Some non-limiting examples of $R^{15}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{15}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{15}$ may be H.

With respect to any relevant formula or structural depiction above, $R^{16}$ may be H or any substituent. Some non-limiting examples of $R^{16}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{16}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{16}$ may be H.

With respect to any relevant formula or structural depiction above, $R^{17}$ may be H or any substituent. Some non-limiting examples of $R^{17}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{17}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{17}$ may be H.

With respect to any relevant formula or structural depiction above, $R^{18}$ may be H or any substituent. Some non-limiting examples of $R^{18}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{18}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{18}$ may be H.

With respect to any relevant formula or structural depiction above, $R^{19}$ may be H or any substituent. Some non-limiting examples of $R^{19}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{19}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{19}$ may be H.

With respect to any relevant formula or structural depiction above, $R^{20}$ may be H or any substituent. Some non-limiting examples of $R^{20}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{20}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{20}$ may be H.

With respect to any relevant formula or structural depiction above, $R^{21}$ may be H or any substituent. Some non-limiting examples of $R^{21}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{21}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{21}$ may be H.

With respect to any relevant formula or structural depiction above, $R^{22}$ may be H or any substituent. Some non-limiting examples of $R^{22}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{22}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{22}$ may be H.

With respect to any relevant formula or structural depiction above, $R^{23}$ may be H or any substituent. Some non-limiting examples of $R^{23}$ may include $R^A$, F, Cl, CN, $OR^A$, $CF_3$, $NO_2$, $NR^A R^B$, $COR^A$, $CO_2R^A$, $OCOR^A$, etc. In some embodiments, $R^{23}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{23}$ may be H.

With respect to any relevant formula or structural depiction above, $R^{24}$ may be H or any substituent. Some non-limiting examples of $R^{24}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{24}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{24}$ may be H.

With respect to any relevant formula or structural depiction above, $R^{25}$ may be H or any substituent. Some non-limiting examples of $R^{25}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{25}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{25}$ may be H.

With respect to any relevant formula or structural depiction above, $R^{26}$ may be H or any substituent. Some non-limiting examples of $R^{26}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{26}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{26}$ may be H.

With respect to any relevant formula or structural depiction above, $R^{27}$ may be H or any substituent. Some non-limiting examples of $R^{27}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{27}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{27}$ may be H.

With respect to any relevant formula or structural depiction above, $R^{28}$ may be H or any substituent. Some non-limiting examples of $R^{28}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{28}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{28}$ may be H.

With respect to any relevant formula or structural depiction above, $R^{29}$ may be H or any substituent. Some non-limiting examples of $R^{29}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{29}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{29}$ may be H.

With respect to any relevant formula or structural depiction above, $R^{30}$ may be H or any substituent. Some non-limiting examples of $R^{30}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{30}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{30}$ may be H.

With respect to any relevant formula or structural depiction above, $R^{31}$ may be H or any substituent. Some non-limiting examples of $R^{31}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{31}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{31}$ may be H.

With respect to any relevant formula or structural depiction above, $R^{32}$ may be H or any substituent. Some non-limiting examples of $R^{32}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{32}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{32}$ may be H.

With respect to any relevant formula or structural depiction above, $R^{33}$ may be H or any substituent. Some non-limiting examples of $R^{33}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{33}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{33}$ may be H.

With respect to any relevant formula or structural depiction above, $R^{34}$ may be H or any substituent. Some non-limiting examples of $R^{34}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{34}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{34}$ may be H.

With respect to any relevant formula or structural depiction above, $R^{35}$ may be H or any substituent. Some non-limiting examples of $R^{35}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{35}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{35}$ may be H.

With respect to any relevant formula or structural depiction above, $R^{36}$ may be H or any substituent. Some non-limiting examples of $R^{36}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{36}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{36}$ may be H.

With respect to any relevant formula or structural depiction above, $R^{37}$ may be H or any substituent. Some non-limiting examples of $R^{37}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{37}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{37}$ may be H.

With respect to any relevant formula or structural depiction above, $R^{38}$ may be H or any substituent. Some non-limiting examples of $R^{38}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{38}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{38}$ may be H.

With respect to any relevant formula or structural depiction above, $R^{39}$ may be H or any substituent. Some non-limiting examples of $R^{39}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{39}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{39}$ may be H.

With respect to any relevant formula or structural depiction above, $R^{40}$ may be H or any substituent. Some non-limiting examples of $R^{40}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{40}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{40}$ may be H.

With respect to any relevant formula or structural depiction above, $R^{41}$ may be H or any substituent. Some non-limiting examples of $R^{41}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{41}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{41}$ may be H.

With respect to any relevant formula or structural depiction above, $R^{42}$ may be H or any substituent. Some non-limiting examples of $R^{42}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{42}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{42}$ may be H.

With respect to any relevant formula or structural depiction above, $R^{43}$ may be H or any substituent. Some non-limiting examples of $R^{43}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{43}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{43}$ may be H.

With respect to any relevant formula or structural depiction above, $R^{44}$ may be H or any substituent. Some non-limiting examples of $R^{44}$ may include $R^A$, F, Cl, CN, $OR^A$, $CF_3$, $NO_2$, $NR^A R^B$, $COR^A$, $CO_2 R^A$, $OCOR^A$, etc. In some embodiments, $R^{44}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{44}$ may be H.

With respect to any relevant formula above, such as Formula 5 or 11, in some embodiments $R^1$, $R^2$, $R^3$, $R^4$, $R^5$, $R^6$, $R^7$, $R^8$, $R^9$, and $R^{10}$ are independently H or $C_{1-6}$ alkyl.

With respect to any relevant formula above, such as Formula 5, 6 Formula 11, 13, or 14, in some embodiments $R^3$ and $R^8$ are $CH_3$.

With respect to any relevant formula above, such as Formula 6, 13, or 14, in some embodiments $R^1$, $R^2$, $R^3$, $R^4$, $R^7$, $R^8$, <$R^9$, and $R^{10}$ are independently H or $C_{1-6}$ alkyl.

With respect to any relevant formula above, such as Formula 7, 8, or 12, in some embodiments $R^1$, $R^2$, $R^3$, $R^4$, $R^5$, $R^6$, $R^7$, $R^8$, $R^{37}$, $R^{38}$, $R^{39}$, and $R^{40}$ are independently H or $C_{1-6}$ alkyl.

With respect to any relevant formula above, such as Formula 9, 11, 12, 13, or 14, in some embodiments $R^{11}$, $R^{12}$, $R^{13}$, and $R^{14}$ are independently H or $C_{1-6}$ alkyl.

With respect to any relevant formula above, such as Formula 10, 11, 12, 13, 14, or 15, in some embodiments $R^{15}$, $R^{16}$, $R^{17}$, and $R^{18}$ are independently H or $C_{1-6}$ alkyl.

With respect to any relevant formula above, such as Formula 11, in some embodiments $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, and $R^{36}$ are independently H or $C_{1-6}$ alkyl.

With respect to any relevant formula above, such as Formula 12, in some embodiments $R^1$, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$ and $R^{44}$ are independently H or $C_{1-6}$ alkyl.

With respect to any relevant formula above, such as Formula 13, in some embodiments $R^1$, $R^2$, $R^3$, $R^4$, $R^7$, $R^8$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, and $R^{36}$ are independently H or $C_{1-6}$ alkyl.

With respect to any relevant formula above, such as Formula 14, in some embodiments $R^1$, $R^2$, $R^3$, $R^4$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{33}$, $R^{34}$, K $R^{35}$, and $R^{36}$ are independently H or $C_{1-6}$ alkyl.

Some embodiments include a composition comprising a compound of any of the formulas above (hereinafter referred to as "a subject compound"). A composition comprising a subject compound may further comprise a fluorescent compound or a phosphorescent compound, and may be useful for light emission in devices such as organic light-emitting devices.

In some embodiments, a composition comprising a subject compound may be a first layer disposed between a second layer and a third layer, wherein the first layer is configured to transport holes from the second layer to the third layer.

In some embodiments, an organic light-emitting device comprises a subject compound. For example, an organic component comprising a subject compound may be disposed between an anode and a cathode. The organic component may further comprise an emissive layer, wherein a subject compound is in the emissive layer. In some embodiments, the organic component comprises at least one layer comprising a subject compound, wherein the layer is configured to transport or inject holes. For example, a layer comprising a subject compound may be a hole-transport layer, a hole-injecting layer, or a hole-injecting and hole-transport layer. In some embodiments, the device is configured so that electrons can be transferred from the cathode to the organic component.

An organic light-emitting device may comprise an organic light-emitting diode (OLED) schematically represented in FIG. 1. Such an OLED may comprise the following layers in the order given: an anode 5, a hole-injection layer 10, a hole-transport layer 15, a light-emitting layer 20, an electron-transport layer 30, and a cathode 35.

An anode, e.g. anode 5, may be a layer comprising a conventional material such as a metal, mixed metal, alloy, metal oxide or mixed-metal oxide, conductive polymer, and/or an inorganic material such as carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag, or alloys thereof; or mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in "Flexible light-emitting diodes made from soluble conducting polymer," Nature, vol. 357, pp. 477-479 (11 Jun. 1992). In some embodiments, the anode layer can have a thickness in the range of about 1 nm to about 1000 nm.

A cathode, e.g. cathode 35, may be a layer including a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

A light-emitting layer, e.g. light-emitting layer 20, may comprise a light-emitting component, and optionally, a host, such as a hole-transport material, an electron-transport material (including a subject compound), or an ambipolar material. If present, the amount of the host in a light-emitting layer may vary. In one embodiment, the amount of a host in a light-emitting layer is in the range of from about 1% to about 99.9% by weight of the light-emitting layer. In another embodiment, the amount of a host in a light-emitting layer is in the range of from about 90% to about 99% by weight of the light-emitting layer. In another embodiment, the amount of a host in a light-emitting layer is about 97% by weight of the light-emitting layer.

In some embodiments, the mass of the light-emitting component is about 0.1% to about 10%, about 1% to about 5%, or about 3% of the mass of the light-emitting layer. In some embodiments, the light-emitting layer may be a neat light-emitting layer, meaning that the light-emitting component is about 100% by weight of the light-emitting layer, or alternatively, the light-emitting layer consists essentially of light-emitting component. The light-emitting component may be a fluorescent and/or a phosphorescent compound. In some embodiments, the light-emitting component comprises a phosphorescent material. In some embodiments, a light-emitting component may include a composition comprising a compound of one of the formulas above and a fluorescent compound or a phosphorescent compound.

A light-emitting component may comprise an iridium coordination compounds such as: bis-{2-[3,5-bis(trifluoromethyl)phenyl]pyridinato-N,C2'}iridium(III)-picolinate; bis(2-[4,6-difluorophenyl]pyridinato-N,C2')iridium (III) picolinate; bis(2-[4,6-difluorophenyl]pyridinato-N,C2')iridium (acetylacetonate); Iridium (III) bis(4,6-difluorophenylpyridinato)-3-(trifluoromethyl)-5-(pyridine-2-yl)-1,2,4-triazolate; Iridium (III) bis(4,6-difluorophenylpyridinato)-5-(pyridine-2-yl)-1H-tetrazolate; bis[2-(4,6-difluorophenyl)pyridinato-N,C$^{2'}$]iridium(III)tetra(1-pyrazolyl)borate; bis[2-(2'-benzothienyl)-pyridinato-N,C3']iridium (III)(acetylacetonate); bis[(2-phenylquinolyl)-N,C2']iridium (III) (acetylacetonate); bis[(1-phenylisoquinolinato-N,C2')]iridium (III) (acetylacetonate); bis[(dibenzo[f, h]quinoxalino-N,C2')iridium (III)(acetylacetonate); Tris(2,5-bis-2'-(9',9'-dihexylfluorene)pyridine)iridium (III); tris[1-phenylisoquinolinato-N,C2']iridium (III); tris-[2-(2'-benzothienyl)-pyridinato-N,C3']iridium (III); tris[1-thiophen-2-ylisoquinolinato-N,C3']iridium (III); tris[1-(9,9-dimethyl-9H-fluoren-2-yl)isoquinolinato-(N,C3')iridium (III)); bis(2-phenylpyridinato-N,C2')iridium(III) (acetylacetonate) [Ir(ppy)$_2$(acac)]; bis(2-(4-tolyl)pyridinato-N,C2')iridium(III)(acetylacetonate) [Ir(mppy)$_2$(acac)]; bis(2-(4-tert-butyl)pyridinato-N,C2')iridium (III) (acetylacetonate) [Ir(t-Buppy)$_2$(acac)]; tris(2-phenylpyridinato-N,C2')iridium (III) [Ir(ppy)$_3$]; bis(2-phenyloxazolinato-N,C2')iridium (III) (acetylacetonate) [Ir(op)$_2$(acac)]; tris(2-(4-tolyl)pyridinato-N,C2')iridium(III) [Ir(mppy)$_3$]; bis[2-phenylbenzthiazolato —N,C2']iridium (III)(acetylacetonate); bis[2-(4-tert-butylphenyl)benzothiazolato-N,C2']iridium(III)(acetylacetonate); bis[(2-(2'-thienyl) pyridinato-N,C3')]iridium (III) (acetylacetonate); tris[2-(9.9-dimethylfluoren-2-yl)pyridinato-(N,C3')]iridium (III); tris [2-(9.9-dimethylfluoren-2-yl)pyridinato-(N,C3')]iridium (III); bis[5-trifluoromethyl-2-[3-(N-phenylcarbzolyl)pyridinato-N,C2']iridium(III)(acetylacetonate); (2-PhPyCz)$_2$Ir (III)(acac); etc.

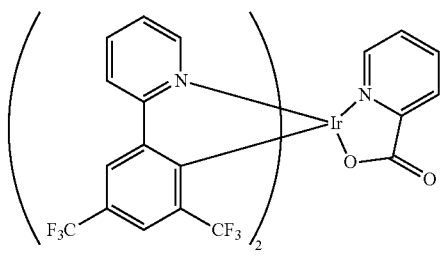

bis-{2-[3,5-bis(trifluoromethyl)phenyl]pyridinato-N,C2'}iridium(III)-picolinate (Ir(CF$_3$ppy)$_2$(Pic))

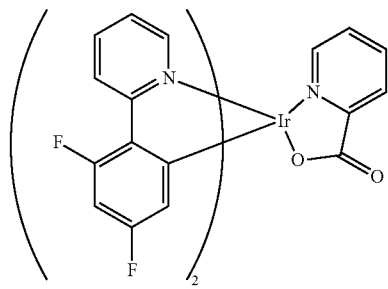

bis(2-[4,6-difluorophenyl]pyridinato-N,C2')iridium (III) picolinate [FIrPic]

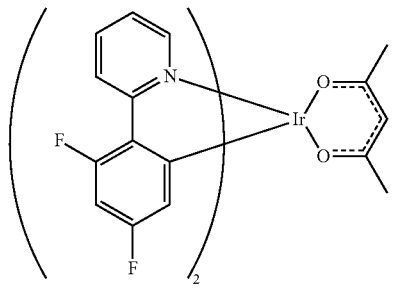

bis(2-[4,6-difluorophenyl]pyridinato-N,C2')iridium(acetylacetonate) [FIr(acac)]

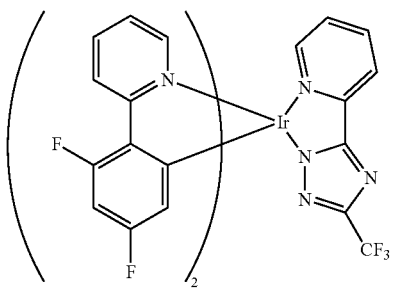

Iridium (III) bis(4,6-difluorophenylpyridinato)-3-(trifluoromethyl)-5-(pyridine-2-yl)-1,2,4-triazolate (FIrtaz)

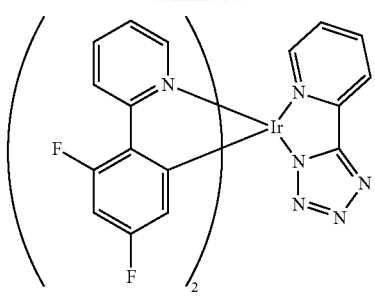
Iridium (III) bis(4,6-difluorophenylpyridinato)-5-(pyridine-2-yl)-1H-tetrazolate (FIrN4)
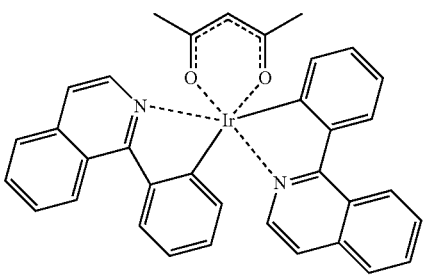
Ir(piq)₂(acac)
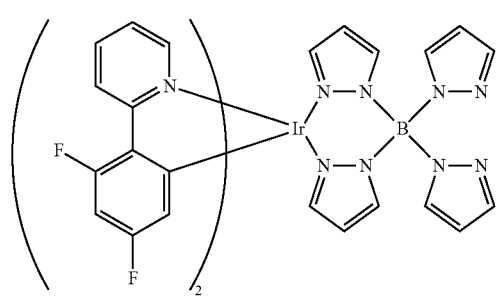
bis[2-(4,6-difluorophenyl)pyridinato-N,C2']iridium(III)tetra(1-pyrazolyl)borate (Fir6)
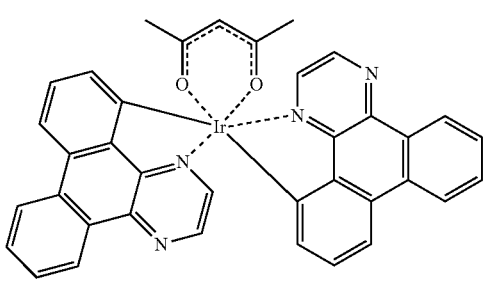
Ir(DBQ)₂(acac)
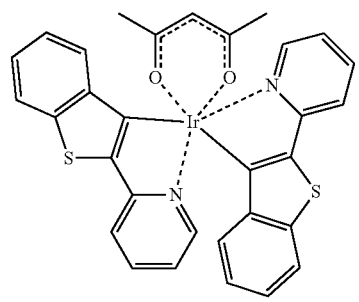
Ir(btp)₂(acac)
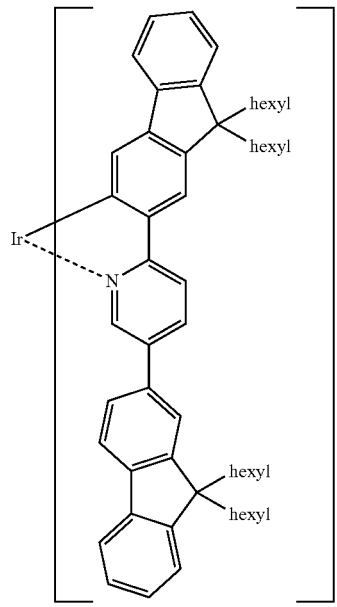
Ir(HFP)₃
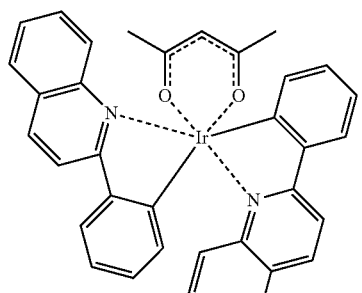
Ir(pq)₂(acac)
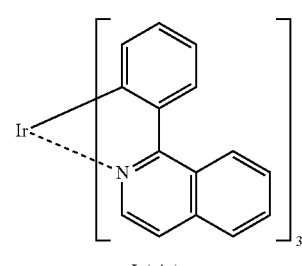
Ir(piq)₃

-continued

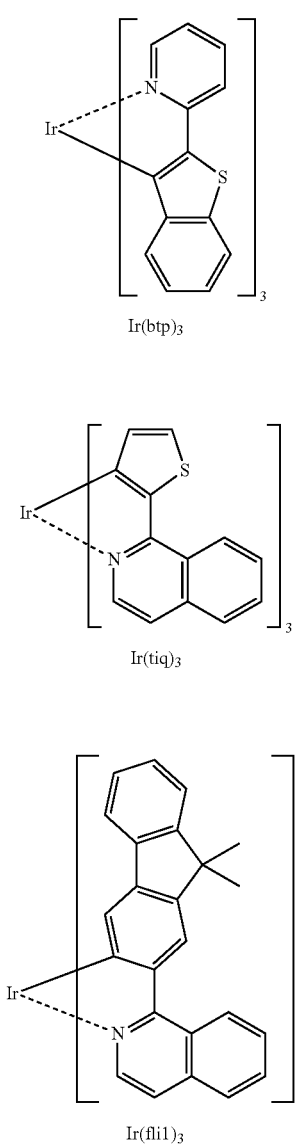

Ir(btp)₃

Ir(tiq)₃

Ir(fli1)₃

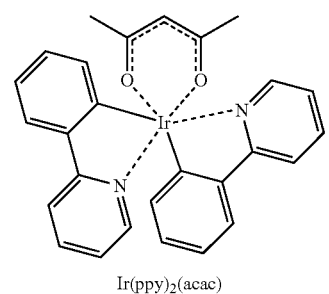

Ir(ppy)₂(acac)

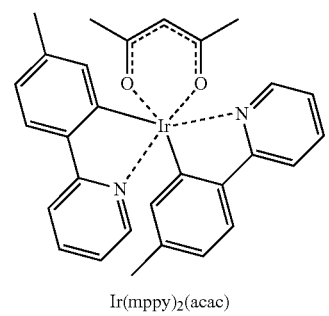

Ir(mppy)₂(acac)

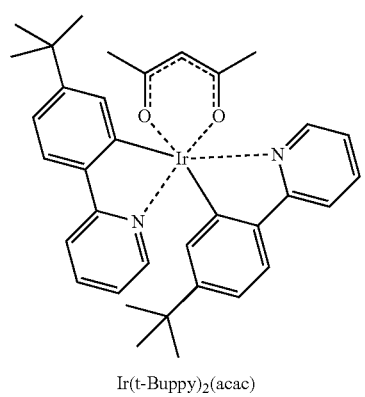

Ir(t-Buppy)₂(acac)

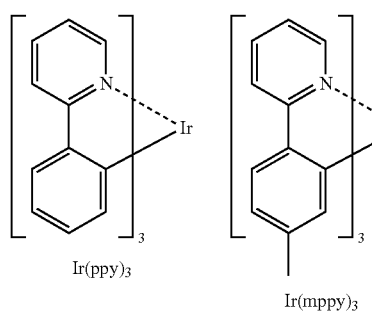

Ir(ppy)₃            Ir(mppy)₃

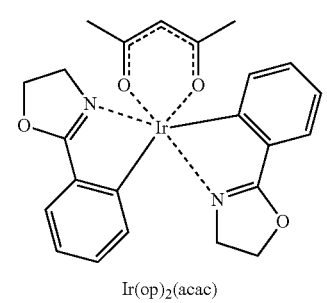

Ir(op)₂(acac)

1. (Btp)₂Ir(III)(acac); bis[2-(2'-benzothienyl)-pyridinato-N, C3']iridium (III)(acetylacetonate)
2. (Pq)₂Ir(III)(acac); bis[(2-phenylquinolyl)-N,C2']iridium (III) (acetylacetonate)
3. (Piq)₂Ir(III)(acac); bis[(1-phenylisoquinolinato-N,C2')] iridium (III) (acetylacetonate)
4. (DBQ)₂Ir(acac); bis[(dibenzo[f, h]quinoxalino-N,C2')iridium (III)(acetylacetonate)
5. [Ir(HFP)₃], tris(2,5-bis-2'-(9',9'-dihexylfluorene)pyridine) iridium (III)
6. Ir(piq)₃; tris[1-phenylisoquinolinato-N,C2']iridium (III)
7. Ir(btp)₃; tris-[2-(2'-benzothienyl)-pyridinato-N,C3']iridium (III)
8. Ir(tiq)₃, tris[1-thiophen-2-ylisoquinolinato-N,C3']iridium (III)
9. Ir(fliq)₃; tris[1-(9,9-dimethyl-9H-fluoren-2-yl)isoquinolinato-(N,C3')iridium (III))

-continued

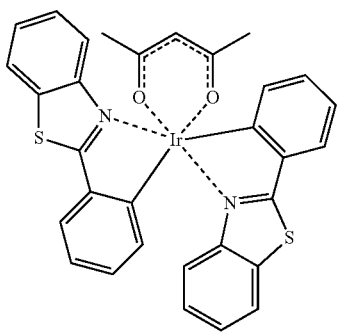

(bt)₂Ir(III)(acac)
Bis[2-
phenylbenzothiazolato-
N,C2'] iridium
(III)(acetylacetonate)

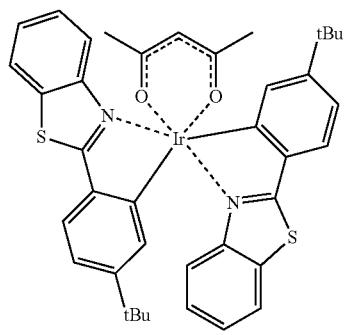

(t-bt)₂Ir(III)(acac)
Bis[2-(4-tert-
butylphenyl)benzothiazolato-
N,C2']iridium(III)
(acetylacetonate)

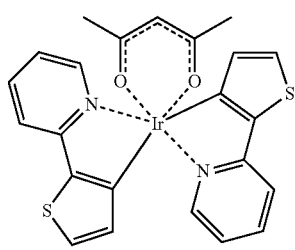

(thp)₂Ir(III)(acac)
Bis[(2-(2'-
thienyl)pyridinato-
N,C3')]iridium (III)
(acetylacetonate)

-continued

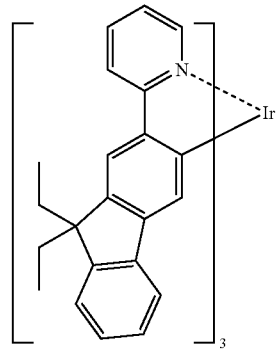

[Ir(Flpy)₃]
Tris[2-(9,9-
dimethylfluoren-2-yl)
pyridinato-
(N,C3')]iridium (III)

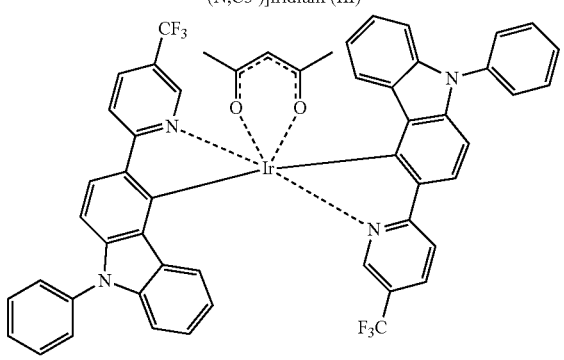

(Cz-CF₃)Ir(III)(acac)
Bis[5-trifluoromethyl-2-[3-(N-
phenylcarbzolyl)pyridinato-
N,C2']iridium(III)(acetylacetonate)

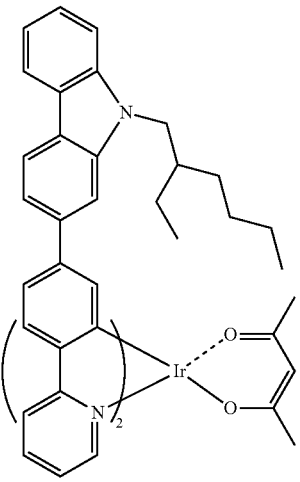

(2-PhPyCz)₂Ir(III)(acac)

The thickness of a light-emitting layer may vary. In one embodiment, a light-emitting layer has a thickness in the range of from about 1 nm to about 150 nm or about 200 nm.

In some embodiments, the organic component may further comprise a hole-transport layer, e.g. hole-transport layer 15, disposed between an anode and a light-emitting layer. The hole-transport layer may comprise at least one hole-transport material, such as a subject compound. Other hole-transport materials may also be included, in addition to or as an alternative to a subject compound, such as an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; an oxadiazole; copper phthalocyanine; 1,1-bis(4-bis (4-methylphenyl)aminophenyl)cyclohexane; 2,9-Dimethyl-4,7-diphenyl-1,10-phenanthroline; 3,5-bis(4-tert-butyl-phenyl)-4-phenyl[1,2,4]triazole; 3,4,5-Triphenyl-1,2,3-triazole; 4,4',4'-tris(3-methylphenylphenylamino) triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino]biphenyl (α-NPD); 4,4',4"-tris (carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); bis[4-(p,p'-ditolyl-amino)phenyl]diphenylsilane (DTASi); 2,2'-bis(4-carbazolylphenyl)-, 1,1'-biphenyl (4Cz-PBP); N,N'N"-1,3,5-tricarbazoloylbenzene (tCP); N,N'-bis (4-butylphenyl)-N,N'-bis(phenyl)benzidine; or the like.

In some embodiments, the organic component may further comprise an electron-transport layer, e.g. electron-transport layer 30, disposed between the cathode and the light-emitting layer. Examples of electron-transport materials may include, but are not limited to, 2-(4-biphenylyl)-5-(4-tert-butylphenyl)-1,3,4-oxadiazole (PBD); 1,3-bis(N,N-t-butyl-phenyl)-1, 3,4-oxadiazole (OXD-7), 1,3-bis[2-(2,2'-bipyridine-6-yl)-1, 3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In one embodiment, the electron transport layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If desired, additional layers may be included in the light-emitting device. These additional layers may include an electron injecting layer (EIL), a hole-blocking layer (HBL), an exciton-blocking layer (EBL), and/or a hole-injecting layer (HIL). In addition to separate layers, some of these materials may be combined into a single layer.

In some embodiments, a light-emitting device can include an electron-injecting layer between a cathode layer and a light-emitting layer. Other suitable electron injecting materials may also be included, and are known to those skilled in the art. Examples of suitable material(s) that can be included in the electron injecting layer include but are not limited to, an optionally substituted compound selected from the following: aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato) zinc. In one embodiment, the electron injecting layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris [N-phenylbenzimidazol-z-yl]benzene (TPBI), or a derivative or a combination thereof.

In some embodiments, a device can include a hole-blocking layer, e.g., between a cathode and a light-emitting layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis (4-bis(4-methylphenyl)aminophenyl)-cyclohexane.

In some embodiments, a light-emitting device can include an exciton-blocking layer, e.g., between a light-emitting layer and an anode. In an embodiment, the band gap of the material(s) that comprise exciton-blocking layer is large enough to substantially prevent the diffusion of excitons. A number of suitable exciton-blocking materials that can be included in the exciton-blocking layer are known to those skilled in the art. Examples of material(s) that can compose an exciton-blocking layer include an optionally substituted compound selected from the following: aluminum quinolate ($Alq_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, a light-emitting device can include a hole-injecting layer, e.g., between a light-emitting layer and an anode. A hole-injecting layer may comprise a subject compound as a hole-injecting material. Other examples of suitable hole-injecting material(s) include, but are not limited to, an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenyl-benzidine, poly(N,N'-bis(4-butylphenyl)-N,N'-bis(phenyl) benzidine), a triphenyl amine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), and a phthalocyanine metal complex derivative such as phthalocyanine copper.

Light-emitting devices comprising a subject compound can be fabricated using techniques known in the art, as informed by the guidance provided herein. For example, a glass substrate can be coated with a high work functioning metal such as ITO which can act as an anode. After patterning the anode layer, a hole-injecting and/or hole-transport layer may be deposited on the anode in that order. The hole-injecting and/or hole-transport layer may comprise a subject compound. A light-emitting layer that includes a light-emitting component, can be deposited on the anode, the hole-transport layer, or the hole-injecting layer. The light-emitting layer may contain a subject compound. An electron-transport layer and/ or an electron-injecting layer may deposited in that order on the light-emitting component. The cathode layer, comprising a low work functioning metal (e.g., Mg:Ag), can then be deposited, e.g., by vapor deposition or sputtering. The device may also contain an exciton-blocking layer, an electron blocking layer, a hole blocking layer, a second light-emitting layer, or other layers that can be added to the device using suitable techniques.

EXAMPLE 1
Synthetic procedures for JC-HT-1 to JC-HT-4
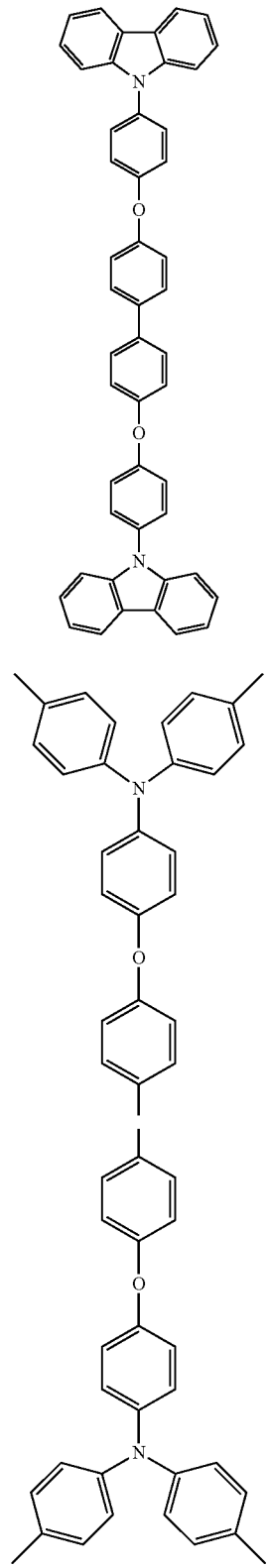
JC-HT1
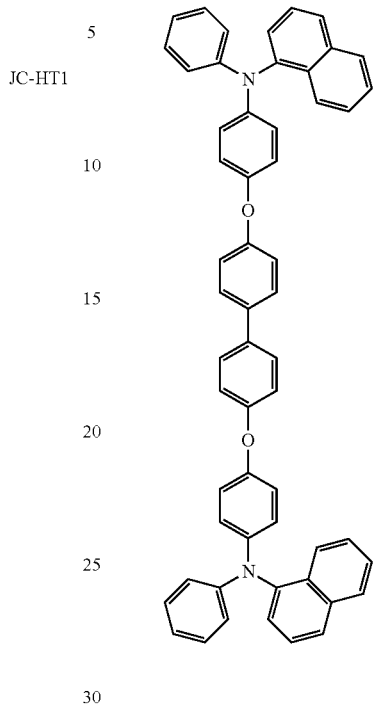
JC-HT3
JC-HT2
JC-HT4

Synthesis procedure of HT-1

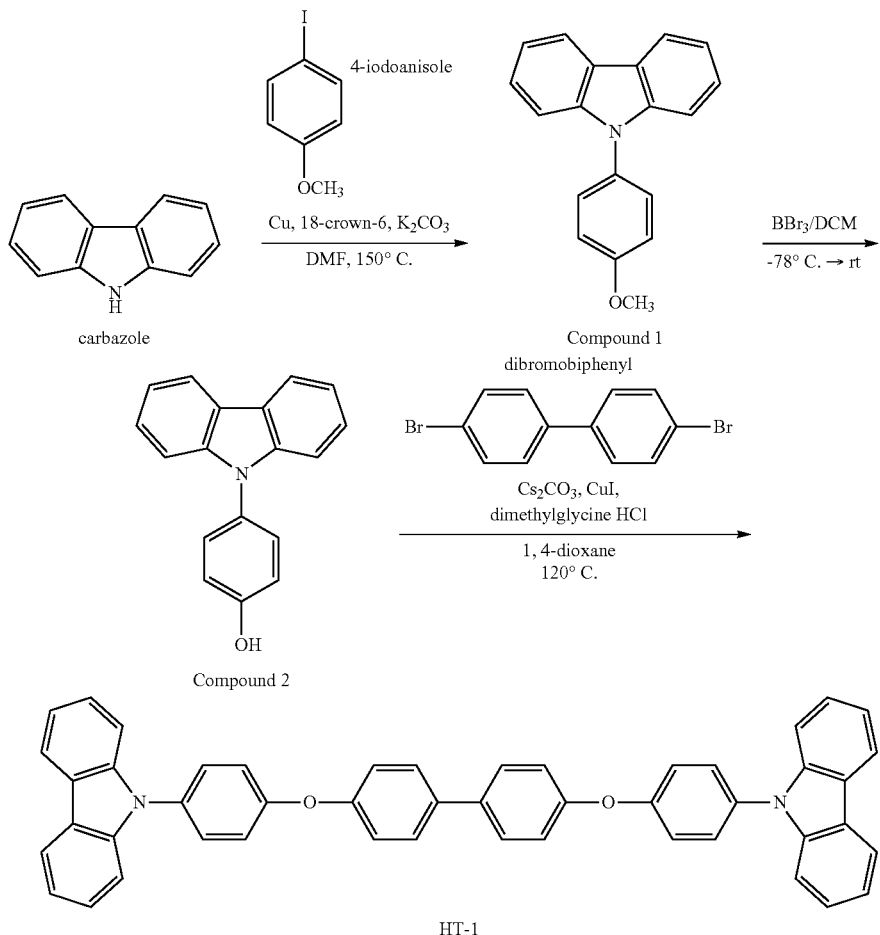

9-(4-methoxyphenyl)-9H-carbazole (Compound 1): A mixture of carbazole (10.0 g, 60.2 mmol), 4-iodoanisole (21.1 g, 90.4 mmol), copper powder (28.58 g, 450 mmol), 1,4,7,10,13,16-hexaoxacyclooctadecane (18-Crown-6) (9.33 g, 35.3 mmol), and potassium carbonate (62.1 g, 450 mmol) was degassed in dimethylformamide (DMF) (anhydrous, 100 mL) for about 45 minutes. The resulting mixture was heated to about 150° C. overnight under argon. After cooling, the mixture was poured into methylene chloride (500 mL). Remaining copper and salts were filtered off. The filtrate was then washed with water (2×200 mL). The organic layer was collected, dried over sodium sulfate, and loaded onto silica gel. A flash column (gradient of 3-5% ethyl acetate in hexanes) and precipitation from methylene chloride/hexanes gave 11.71 g (71% yield) of product (Compound 1).

4-(9H-carbazol-9-yl)phenol (Compound 2): Compound 1 (11.63 g, 42.6 mmol) was dissolved in methylene chloride and the solution was cooled to about −77° C. Boron tribromide (BBr$_3$) (45 mL of a 1M solution) was added dropwise to the cold solution. The solution was stirred overnight under argon while slowly warming to room temperature. LCMS showed a single peak with desired mass (M$^-$=528). Methanol (100 mL) was then added to reaction mixture; and the mixture was stirred for about 30 minutes. The whole was then loaded onto silica gel. A flash column (gradient of 10-20% ethyl acetate in hexanes) gave 10.94 g of material (Compound 2) (99% yield).

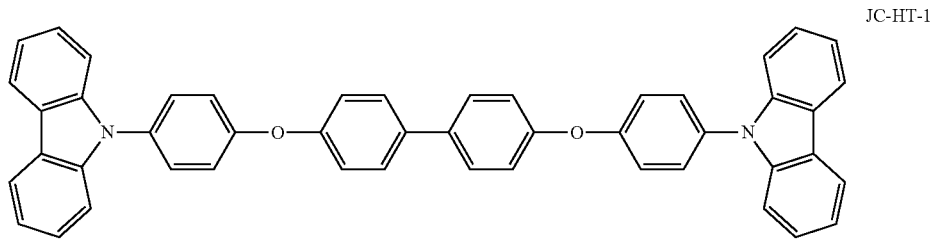 [SMILES: c1ccc2c(c1)c1ccccc1n2-c1ccc(Oc2ccc(-c3ccc(Oc4ccc(-n5c6ccccc6c6ccccc65)cc4)cc3)cc2)cc1]

JC-HT-1

Compound HT-1: A mixture of Compound 2 (10.0 g, 8.3 mmol), 4, 4'-dibromobiphenyl (24.1 g, 77.2 mmol), cesium carbonate ($Ce_2CO_3$) (25.2 g, 77.2 mmol), copper iodide (CuI) (700 mg, 3.86 mmol), and dimethylglycine hydrochloride (1.62 g, 11.6 mmol) was degassed in 1,4-dioxane (anhydrous, 100 mL) for about 45 minutes. The mixture was heated to about 120° C. overnight under argon. After cooling, the mixture was poured into methylene chloride (300 mL) the subsequent mixture was washed with water and brine. The organic layer was collected, dried over sodium sulfate, and loaded onto silica gel. A plug using 10% ethyl acetate in hexanes was used to remove baseline impurities. A subsequent flash column (5% toluene in hexanes), and precipitation from methylene chloride/methanol gave 2.0 g of product (HT-1) (in 8% yield), confirmed by LCMS (APCI+); calcd for $C_{48}H_{33}N_2O_2$ (M+H): 669. Found: 669.

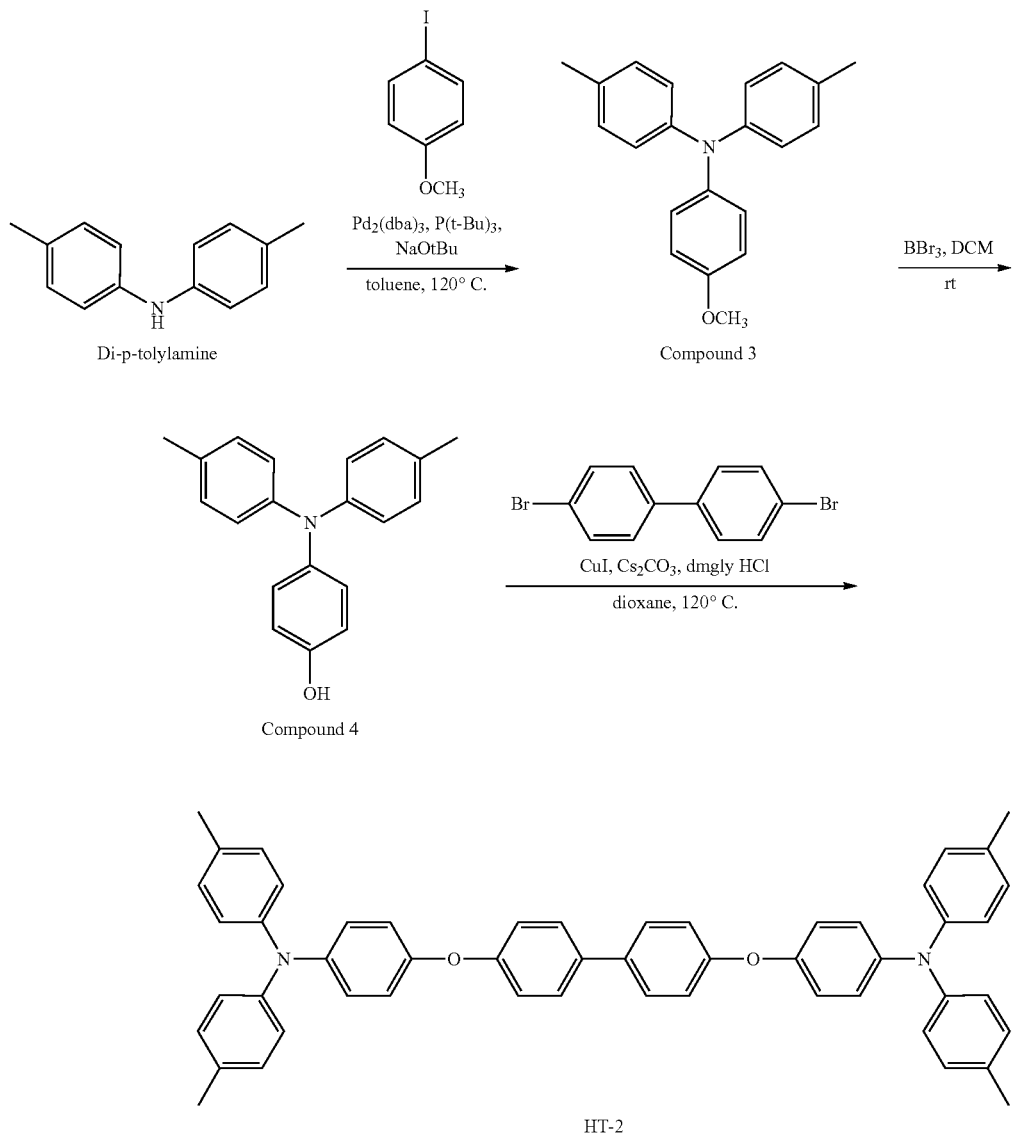

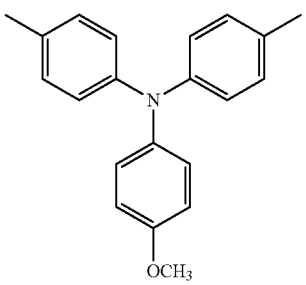

Compound 3

4-Methoxy-N,N-di-p-tolylaniline (Compound 3): A mixture of tris(dibenzylideneacetone)dipalladium (Pd$_2$(dba)$_3$) (60 mg, catalytic), and tri-tert-butyl phosphine (P(tBu)$_3$) (5 mL of a 10% solution in hexanes) was degassed in toluene (anhydrous, 60 mL) for about 20 minutes. Di-p-tolylamine (4.0 g, 20.3 mmol), and 4-iodoanisole (11.88 g, 50.8 mmol) were added and degassing continued for about 15 minutes. Sodium tert-butoxide (NaOtBu) (2.4 g, 25 mmol) was added, and the mixture was further degassed for about 10 minutes. The whole was heated overnight at about 120° C. under argon. After cooling, the mixture was poured into ethyl acetate and washed with water (2×200 mL). The organic layer was collected and dried over sodium sulfate, then loaded onto silica gel. A flash column (gradient of 2-3% ethyl acetate in hexanes) gave 3.26 g of material (Compound 3) (53% yield).

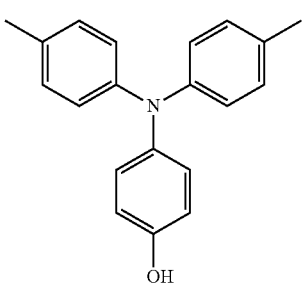

Compound 4

4-(Di-p-tolylamino)phenol (Compound 4): Compound 3 (3.05 g, 10.1 mmol) was dissolved in methylene chloride (anhydrous, 50 mL) and the solution was cooled to about −77° C. Boron tribromide (12 mL of a 1M solution) was added dropwise to the cold solution. The whole was stirred and slowly warmed to room temperature overnight under argon. LCMS shows single desired mass of 288 (M⁻). The mixture was poured into methanol (200 mL) and stirred for about 45 minutes. The mixture was then concentrated under vacuum. Then, methylene chloride (100 mL) was added. The solution was then washed with water (2×200 mL). The organic layer was collected, dried over sodium sulfate, and concentrated under vacuum. Precipitation using hexanes gave 2.44 g of material (Compound 4) (84% yield).

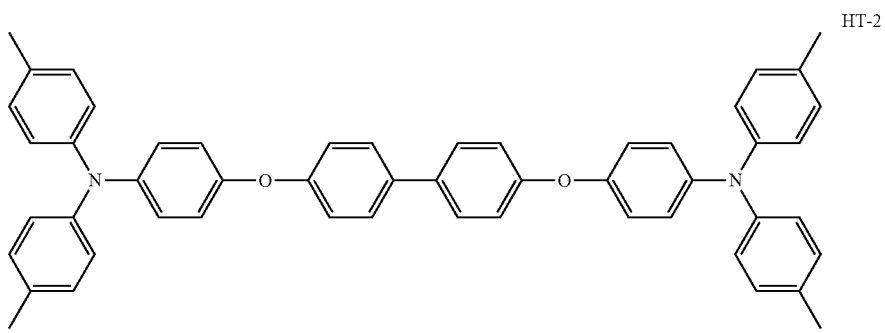 [SMILES: Cc1ccc(N(c2ccc(C)cc2)c2ccc(Oc3ccc(-c4ccc(Oc5ccc(N(c6ccc(C)cc6)c6ccc(C)cc6)cc5)cc4)cc3)cc2)cc1]

HT-2

Compound HT-2: A mixture of Compound 4 (2.4 g, 8.3 mmol), 4, 4'-dibromobiphenyl (1.25 g, 4.0 mmol), cesium carbonate (5.41 g, 16.6 mmol), copper iodide (158 mg, 0.83 mmol), and dimethylglycine hydrochloride (348 mg, 2.49 mmol) was degassed in 1,4-dioxane (anhydrous, 40 mL) for about 45 minutes. The mixture was heated to about 120° C. overnight under argon. After cooling, the mixture was poured into methylene chloride (300 mL), and the subsequent mixture was washed with water and brine. The organic layer was collected, dried over sodium sulfate, and loaded onto silica gel. A flash column (gradient of 5-20% methylene chloride in hexanes), and precipitation from methylene chloride/hexanes gave 480 mg of product (Compound HT-2) (in 16% yield), confirmed by LCMS (APCI+). Calcd for $C_{52}H_{45}N_2O_2$ (M+H): 729. Found: 729.

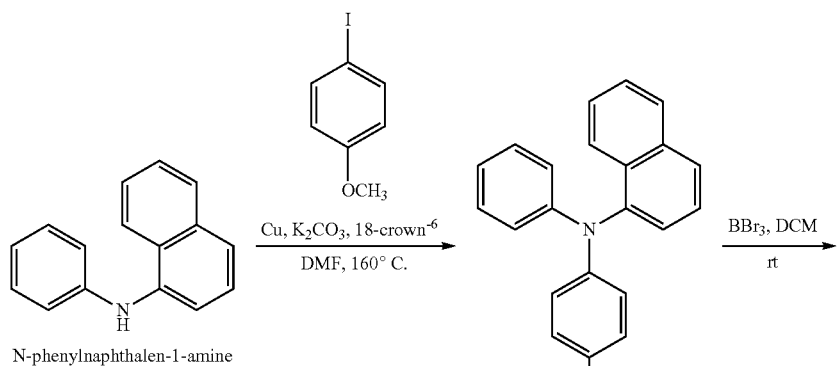

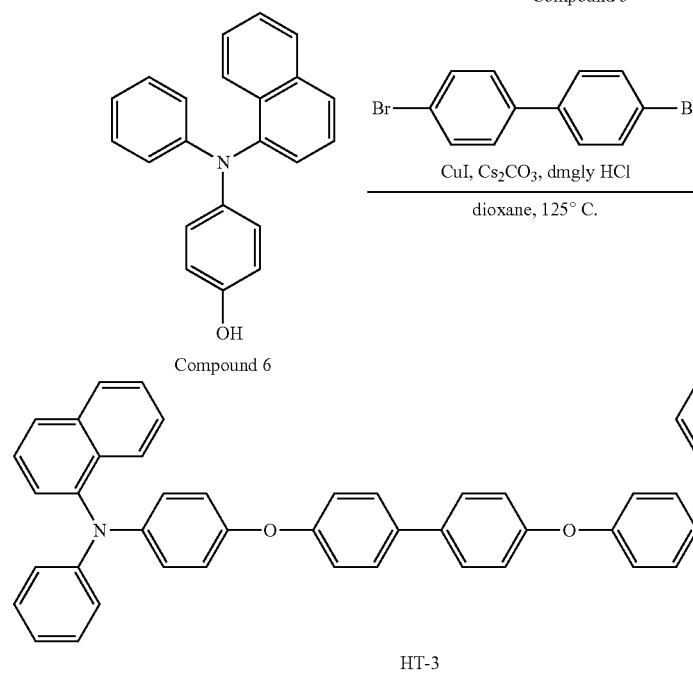

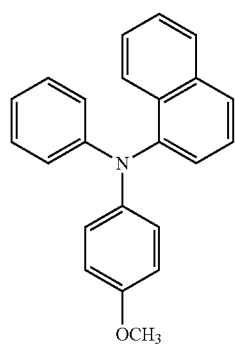

Compound 5

N-(4-methoxyphenyl)-N-phenylnaphthalen-1-amine (Compound 5): A mixture of N-phenylnaphthalen-1-amine (5.0 g, 22.8 mmol), 4-iodoanisole (8.0 g, 34.2 mmol), copper powder (2.89 g, 45.6 mmol), $K_2CO_3$ (12.59 g, 91.2 mmol) and 18-crown-6 (0.607 g, 2.3 mmol) in DMF (200 mL) was degassed and heated to reflux for overnight under argon. After the salt and copper were filtered off, the solution was poured into water (300 mL), and extracted with DCM (2×300 mL). The organic phase was combined and washed with brine, dried over $Na_2SO_4$, loaded on silica gel, purified by flash column (5 to 20% DCM in hexanes). The desired fraction was collected, concentrated, and recrystallized in ethyl acetate/methanol to obtain a white solid (Compound 5) (2.59 g, in 35% yield).

Compound 6

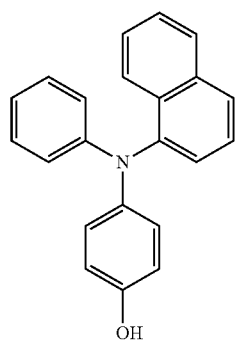

4-(naphthalen-1-yl(phenyl)amino)phenol (Compound 6): To a solution of Compound 5 (2.58 g, 7.93 mmol) in DCM (50 mL) was slowly added BBr₃ (8.5 mL, 8.5 mmol) at about −78° C. The resulting mixture was stirred overnight under argon while slowly warming up to room temperature. Methanol (60 mL) was added into the flask, and the mixture was stirred for about 3 hours. After concentration to 20 mL, the mixture was poured into DCM (200 mL), then washed with water, brine, and dried over Na₂SO₄, loaded on silica gel, and purified by flash column (hexanes/ethyl acetate 8:1 to 3:1). The desired fraction was concentrated to give a white solid (Compound 6) (1.84 g, in 77% yield).

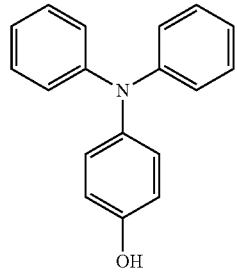

Compound 7

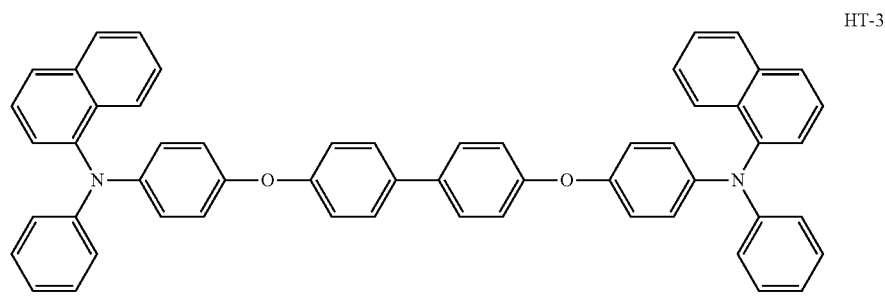 [SMILES: c1ccc(N(c2ccc(Oc3ccc(-c4ccc(Oc5ccc(N(c6ccccc6)c6cccc7ccccc67)cc5)cc4)cc3)cc2)c2cccc3ccccc23)cc1]

HT-3

Compound HT-3: A mixture of Compound 6 (1.63 g, 5.23 mmol), 4,4'-dibromobiphenyl (0.544 g, 1.74 mmol), CuI (0.066 g, 0.348 mmol), N,N-dimethylglycine hydrochloride (0.146 g, 1.04 mmol), Cs₂CO₃ (2.27 g, 6.96 mmol) in dioxane (100 mL), was degassed using freeze-pump-thaw method, then heated to 125° C. overnight under argon. After cooling, mixture was poured into DCM (100 mL), the solid was filtered off. Filtrate was washed using water and brine. The organic phase was collected and dried over Na₂SO₄, loaded on silica gel, then purified by flash column using hexane/ethyl acetate (20:1 to 9:1). Desired fractions were collected, concentrated, and recrystallized in ethyl acetate/methanol gave a white solid (HT-3) (0.89 g, in 66% yield). Confirmed by LCMS (APCI+): calcd for $C_{56}H_{41}N_2O_2$ (M+H): 773. Found: 773.

4-(diphenylamino)phenol (Compound 7): To a solution of 4-methoxy-N,N-diphenylaniline (6.0 g, 21.8 mmol) in DCM (40 mL) was slowly added BBr₃ (23 mL, 23 mmol) at about −78° C. The mixture was then stirred overnight under argon while it slowly warmed up to room temperature. To the resulting mixture, methanol (70 mL) was added slowly, then stirred for about 3 hours. The mixture was then poured into water and extracted with DCM (2×200 mL). The organic phases were then combined and washed with brine, dried over Na₂SO₄, loaded on silica gel, and purified by short plug using hexane/ethyl acetate (9:1 to 8:1). The desired fraction was concentrated and washed with hexanes to give a white solid (Compound 7) (4.59 g, in 81% yield).

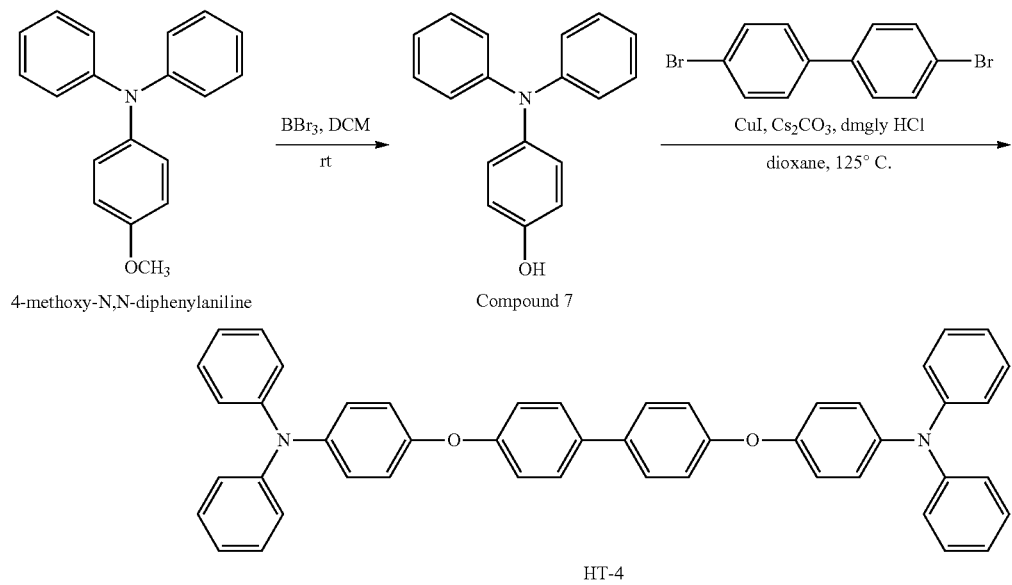

HT-4

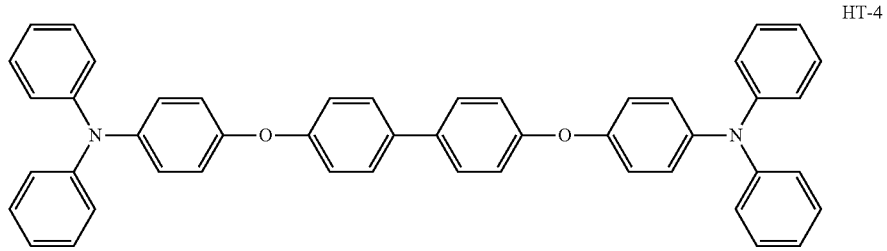 [SMILES: c1ccc(N(c2ccccc2)c2ccc(Oc3ccc(-c4ccc(Oc5ccc(N(c6ccccc6)c6ccccc6)cc5)cc4)cc3)cc2)cc1]

HT-4

Compound HT-4: A mixture of 4-(diphenylamino)phenol (Compound 7) (4.4 g, 16.8 mmol), 4,4'-dibromobiphenyl (1.75 g, 5.61 mmol), CuI (0.214 g, 1.12 mmol), N,N-dimethylglycine hydrochloride (0.47 g, 3.37 mmol), $Cs_2CO_3$ (7.31 g, 22.4 mmol) in dioxane (100 mL) was degassed using freeze-pump-thaw method, then heated to about 125° C. overnight under argon. The mixture was then poured into ethyl acetate (200 mL), the solid was then filtered off. The filtrate was washed with water and brine, loaded on silica gel, and purified by flash column using hexanes/ethyl acetate (50:1 to 40:1). The desired fraction was concentrated and recrystallized in DCM/methanol to give a white solid (HT-4) (2.26 g, in 60% yield). Confirmed by LCMS (APCI+): calcd for $C_{48}H_{37}N_2O_2$ (M+H): 673. Found: 673.

EXAMPLE 2

Photoluminescence (PL) spectra were recorded on a FluoroMax-3 fluorescence spectrophotometer (Horiba Jobin Yvon, Edison, N.J., USA). 2-Methyltetrahydrofuran (2-MeTHF) (Aldrich, spectroscopic grade) was used as received. 2 M (2 mg of sample/1 mL of 2-MeTHF) was prepared and then transferred to quartz tube prior to measurement. Then, the sample was frozen by liquid nitrogen at 77K. Phosphorescent emission spectrum was recorded and the highest-energy vibronic band was determined to calculate triplet (T1) energy level.

Cyclic voltammetry (CV) was carried out in nitrogen-purged anhydrous N,N-dimethylformamide (DMF) (Aldrich) at room temperature with Echo-Chemie potentiostat/galvanostat (Echo Chemie/Metrohm Autolabe B.V., Utrecht, the Netherlands) Tetra-n-butylammonium hexafluorophosphate (TBAPF6) and DMF were purchased from Aldrich and used as received. Supporting electrolyte solution (0.1M) with TBAPF6 and analyte, e.g., BH-3, (0.1 mM) in DMF was used for CV study. Formal potentials were calculated as the average of cyclic voltammetric anodic and cathodic peaks and ferrocenium-ferrocene (Fc+/Fc) as the internal standard was introduced to calibrate HOMO (highest occupied molecular orbital) and LUMO (lowest unoccupied molecular orbital) energy at each experiment. Scan rate of 100 mV/s was used unless otherwise.

Triplet (T1) Energy Calculation:

Triplet energy was recorded on a FloroMax-3 spectrometer (Jobin Yvon Horiba, Edison, N.J.) with phosphorescence spectra at 77K. It was determined by the highest-energy vibronic sub-band of the phosphorescence spectra in substantially the same manner as described in US Patent Publication 2012/0214,269, filed 15 Feb. 2012, Ser. No. 13/397,342).

T1 energy, obtained in the same manner as described above, were 2.77 eV for HT-1, 2.74 eV for HT-2, 2.38 eV for HT-3, and 2.78 eV for HT-4.

HOMO/LUMO Energy Calculation:

HOMO energy was directly determined in substantially the same manner as described in US Patent Publication 2012/0214,269, filed 15 Feb. 2012, Ser. No. 13/397,342 by oxidation potential of HT-1 with respect to redox of ferrocene/ferrocenium in anodic scan in DMF. The potential difference between them was determined to be 0.78 eV. Therefore, using vacuum level of ferrocene as 4.8 eV, HOMO for HT-1 was determined to be −5.58 eV. LUMO energy was determined by equation of band gap Eg(eV)=HOMO−LUMO. Eg (eV) (3.44 eV) was estimated by oneset value of UV-vis spectroscopy and then LUMO was calculated as −2.14 eV.

| Compound | HOMO | LUMO | T1 |
|---|---|---|---|
| JC-HT-1 | −5.58 | −2.14 | 2.77 |
| JC-HT-2 | −5.14 | −1.71 | 2.74 |
| JC-HT-3 | −5.3 | −2.12 | 2.38 |
| JC-HT-4 | −5.29 | −1.79 | 2.78 |

EXAMPLE 3

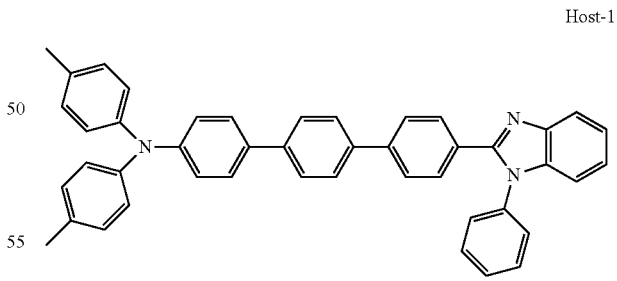

Host-1

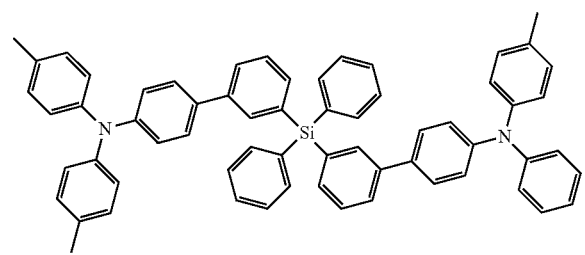 [SMILES: Cc1ccc(N(c2ccccc2)c2ccc(-c3cccc([Si](c4ccccc4)(c4ccccc4)c4cccc(-c5ccc(N(c6ccc(C)cc6)c6ccc(C)cc6)cc5)c4)c3)cc2)cc1]

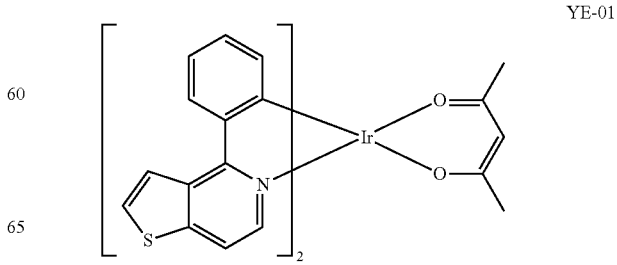

YE-01

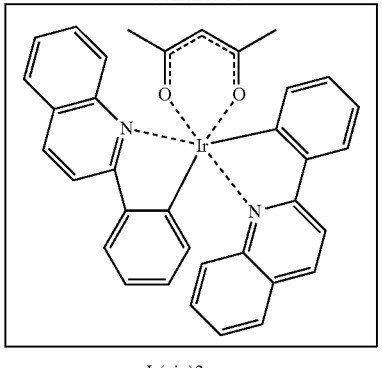

Ir(piq)2acac

Device Fabrication

Figure 2:
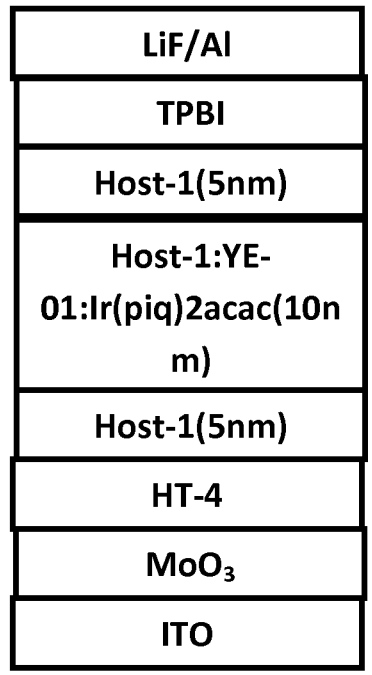
FIG. 2 is schematic diagram of an embodiment of an organic light-emitting diode (OLED).

A device (Device A) was fabricated in the following manner. The ITO substrates having sheet resistance of about 14 ohm/sq were cleaned ultrasonically and sequentially in detergent, water, acetone and then IPA; and then dried in an oven at about 80° C. for about 30 min under ambient environment. Substrates were then baked at about 200° C. for about 1 hour in an ambient environment, then under UV-ozone treatment for about 30 minutes, followed by baking at about 200° C. for about 30 min inside a glove box ($N_2$ environment). The substrate was then be transferred into a vacuum chamber, where a hole injection layer ($MoO_3$) was deposited on top of ITO surface at rate about 0.1 nm/s for about a 10 nm thickness, then HT-4 (hole transporting material) was deposited at a rate of about 0.1 nm/s rate for about a 40 nm thickness. Followed by the deposition of fluorescent blue layer (Host-1) on top of HT-4, yielding a 5 nm thick film, followed by concurrent deposition of Host-1, Ir(PIQ)$_2$(acac) and YE-01 at deposition rates of about 0.1 nm/s, about 0.001 nm/s and about 0.01 nm/s, respectively, to form about a 10 nm thick layer, and deposition of another fluorescent blue (Host-1) layer having a thickness of about 5 nm. Then 1,3,5-tris(N-phenylbenzimidizol-2-yl)benzene (TPBI) at deposition rate about 0.1 nm/s was deposited on the Host-1 layer to form about a 40 nm thick film. LiF (1.0 nm) and Al (100 nm) were then deposited successively at deposition rates of about 0.005 and about 0.2 nm/s, respectively. All the depositions were done at vacuum level of about $2\times10^{-7}$ torr. Each individual device had areas of about 8 mm$^2$ The representative device structure was: ITO (about 150 nm thick)/MoO$_3$ (about 40 nm thick)/HT-4 (about 40 nm thick)/Host-1 (fluorescent blue) (about 5 nm thick)/Host-1: YE-1:Ir(piq)$_2$ (about 10 nm thick)/Host-1 (fluorescent blue) about 5 nm thick)/TPBI (about 30 nm thick)/LiF(about 1 nm thick)/Al (about 100 nm thick). Example configurations of the device comprising a compound described herein are shown in FIGS. 1 and 2. The device comprises the following layers in the order given: an ITO anode 5, a MoO$_3$ hole-injection layer 10, a hole-transport layer 15, a light-emitting layer 20, an electron-transport layer 30, and a LiF/Al cathode 35. In this configuration, the light-emitting layer 20 comprises a first emissive layer, a second emissive layer and a third emissive layer. The first and third emissive layers comprise a fluorescent blue emitting compound, e.g., Host-1 described herein. The second emissive layer comprises Host-1, a yellow (YE-01) and red light-emitting (Ir(piq)$_2$acac) component.

EXAMPLE 4

All spectra were measured with an Ocean Optics HR 4000 spectrometer and I-V-L characteristics were taken with a Keithley 2400 SourceMeter and Newport 2832-C power meter and 818 UV detector. All device operation was performed inside a nitrogen-filled glove-box.

Figure 3:
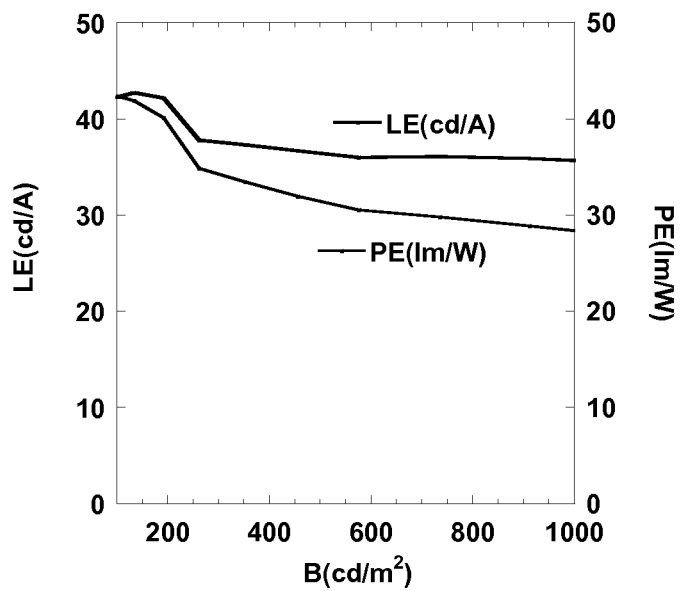
FIG. 3 is a plot of the luminescent efficiency and power efficiency as a function of luminance (B) of Device-A.

It is believed that the best known efficiency for a HY-WOLED is 25 lm/W at 1000 cd/m$^2$, reported by Karl Leo (Adv. Funct. Mater. 2009, 19, 1-15.) FIG. 3 is a plot of the luminescent efficiency and power efficiency as a function of luminance (B) of Device-A, and shows that the efficiency of Device-A at 1000 cd/m2 is about 27 lm/W. Table below shows CIE coordinates, color temperature and the color rendering index CRI of Device 1 at various operating voltages.

| V (V) | CIE (x, y) | Color temperature (K) | CRI |
|---|---|---|---|
| 4 | 0.426, 0.393 | 3090 | 71 |
| 5 | 0.420, 0.389 | 3172 | 71 |
| 6 | 0.407, 0.381 | 3374 | 72 |
| 7 | 0.392, 0.370 | 3639 | 73 |
| 8 | 0.378, 0.361 | 3930 | 75 |

Figure 4:
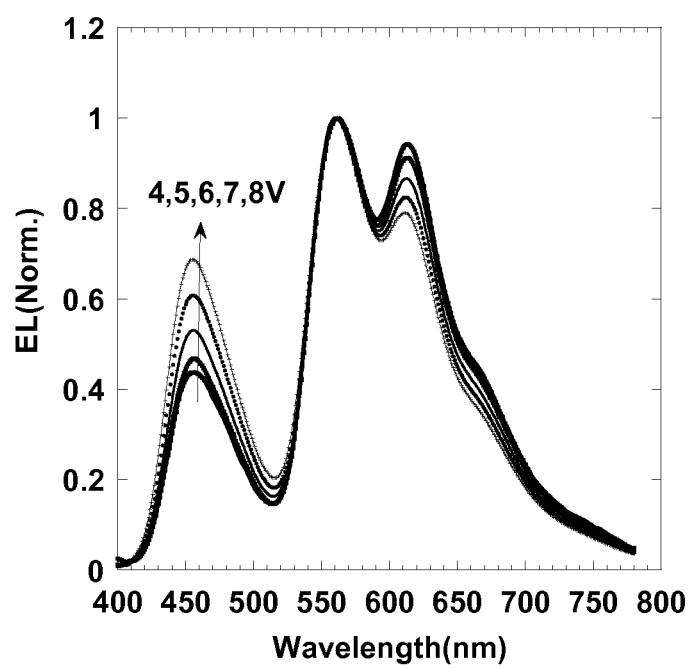
FIG. 4 is a plot of the luminescent efficiency as a function of wavelength with driving currents of 4, 5, 6, 7, and 8V for Device-A.
Figure 5:
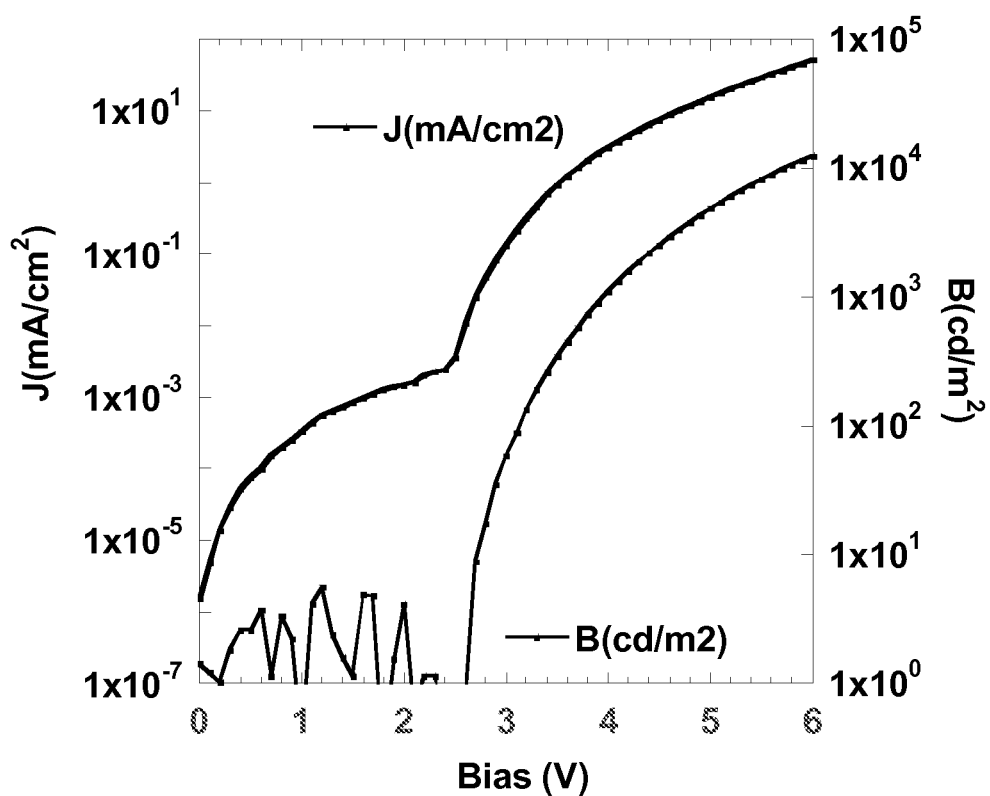
FIG. 5 is a plot of J and luminance (B) as a function of voltage (v) for Device-A.

FIG. 4 is a plot of the luminescent efficiency as a function of wavelength with driving currents of 4, 5, 6, 7, and 8V. FIG. 5 is a plot of J and Brightness (B) as a function of voltage (V). The above data shows benefit of HT-1 as a hole transporting material since a device utilizing the material demonstrates a power efficiency of about 27 lm/W.

What is claimed is:

1. A compound represented by a formula:

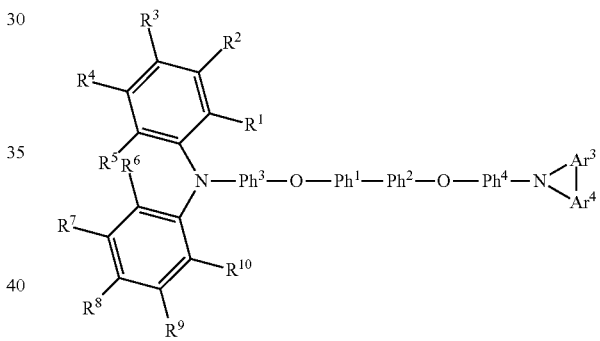

Ph$^1$, Ph$^2$, Ph$^3$, and Ph$^4$, are independently optionally substituted p-phenylene; and Ar$^3$, and Ar$^4$, are independently optionally substituted phenyl or optionally substituted naphthyl, wherein each substituent of Ar$^3$ and Ar$^4$ is independently C$_{1-6}$ alkyl; and wherein R$^1$, R$^2$, R$^3$, R$^4$, R$^5$, R$^6$, R$^7$, R$^8$, R$^9$, and R$^{10}$ are independently H or C$_{1-6}$ alkyl.

2. The compound of claim 1, wherein R$^3$ and R$^8$ are CH$_3$.

3. A compound represented by a formula:

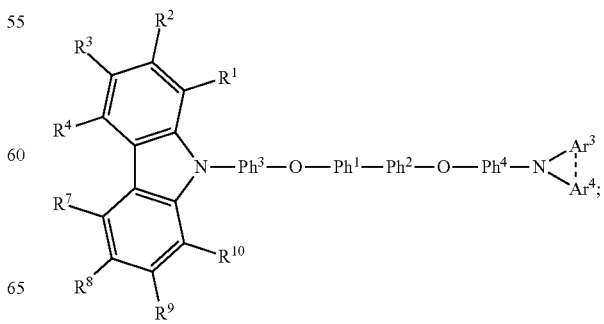

wherein each dashed line is independently an optional bond;

Ph$^1$, Ph$^2$, Ph$^3$, and Ph$^4$, are independently optionally substituted p-phenylene; and Ar$^3$, and Ar$^4$, are independently optionally substituted phenyl or optionally substituted naphthyl, wherein each substituent of Ar$^3$ and Ar$^4$ is independently C$_{1-6}$ alkyl; and wherein R$^1$, R$^2$, R$^3$, R$^4$, R$^7$, R$^8$, R$^9$, and R$^{10}$ are independently H or C$_{1-6}$ alkyl.

4. A compound represented by a formula:

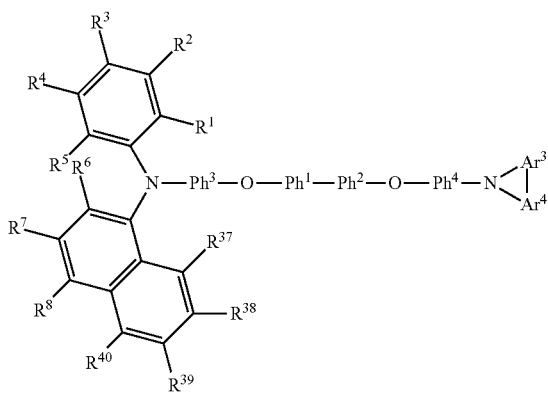

Ph$^1$, Ph$^2$, Ph$^3$, and Ph$^4$, are independently optionally substituted p-phenylene; and Ar$^3$, and Ar$^4$, are independently optionally substituted phenyl or optionally substituted naphthyl, wherein each substituent of Ar$^3$ and Ar$^4$ is independently C$_{1-6}$ alkyl; and wherein R$^1$, R$^2$, R$^3$, R$^4$, R$^5$, R$^6$, R$^7$, R$^8$, R$^{37}$, R$^{38}$, R$^{39}$, and R$^{40}$ are independently H or C$_{1-6}$ alkyl.

5. A compound represented by a formula:

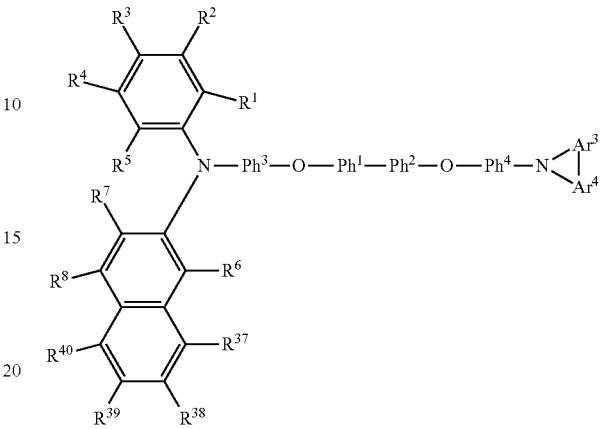

Ph$^1$, Ph$^2$, Ph$^3$, and Ph$^4$, are independently optionally substituted p-phenylene; and Ar$^3$, and Ar$^4$, are independently optionally substituted phenyl or optionally substituted naphthyl, wherein each substituent of Ar$^3$ and Ar$^4$ is independently C$_{1-6}$ alkyl; and wherein R$^1$, R$^2$, R$^3$, R$^4$, R$^5$, R$^6$, R$^7$, R$^8$, R$^{37}$, R$^{38}$, R$^{39}$, and R$^{40}$ are independently H or C$_{1-6}$ alkyl.

6. The compound of claim 3, further represented by a formula:

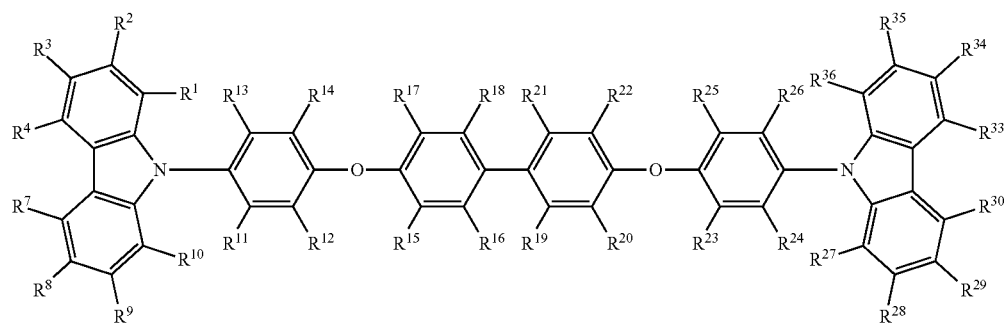

wherein R$^1$, R$^2$, R$^3$, R$^4$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{33}$, R$^{34}$, R$^{35}$, and R$^{36}$ are independently H or C$_{1-6}$ alkyl.

7. A compound represented by a formula:

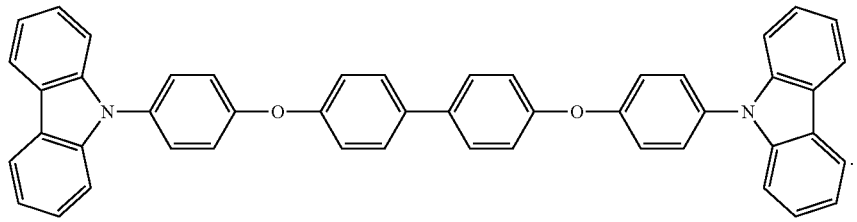 [SMILES: c1ccc2c(c1)c1ccccc1n2-c1ccc(Oc2ccc(-c3ccc(Oc4ccc(-n5c6ccccc6c6ccccc65)cc4)cc3)cc2)cc1]

8. The compound of claim 1, wherein $Ph^1$, $Ph^2$, $Ph^3$, and $Ph^4$ are unsubstituted, or all substituents of $Ph^1$, $Ph^2$, $Ph^3$, and $Ph^4$ have a molecular weight of about 15 g/mol to about 200 g/mol.

9. An organic light-emitting device comprising a compound according claim 1.

10. The device of claim 9, wherein the organic component further comprises an emissive layer, wherein the compound is in the emissive layer.

11. The device of claim 9, wherein the organic component further comprises at least one layer comprising the compound, wherein the layer is configured to transport or inject holes.

12. The device of claim 11, wherein the layer is a hole-transport layer, a hole-injecting layer, or a hole-injecting and hole-transport layer.

13. A composition comprising a compound of claim 7.

14. The composition of claim 13, further comprising a fluorescent compound or a phosphorescent compound.

15. The composition of claim 14, wherein the composition is a first layer disposed between a second layer and a third layer, wherein the first layer is configured to transport holes from the second layer to the third layer.

16. A method of transporting holes between layers comprising:
providing an electrical potential between a first layer and a second layer through a composition comprising a compound according to claim 7.

17. An organic light-emitting device comprising a compound according to claim 3.

18. An organic light-emitting device comprising a compound according to claim 4.

19. An organic light-emitting device comprising a compound according to claim 5.

* * * * *